United States Patent [19]
Letarte et al.

[11] Patent Number: 6,022,687
[45] Date of Patent: Feb. 8, 2000

[54] DIAGNOSIS OF AND THERAPY FOR HEREDITARY HAEMORRHAGIC TELANGIECTASIA

[75] Inventors: Michelle Letarte, Toronto, Canada; Douglas A. Marchuk, Chapel Hill; Kimberly McAllister, Durham, both of N.C.

[73] Assignee: Duke University, Durham, N.C.

[21] Appl. No.: 08/564,496

[22] Filed: Nov. 29, 1995

Related U.S. Application Data

[63] Continuation-in-part of application No. 08/346,129, Nov. 29, 1994.

[51] Int. Cl.[7] .............................. C12Q 1/68; C12P 19/34; C07H 21/04
[52] U.S. Cl. ............................ 435/6; 435/91.2; 435/91.1; 536/24.3
[58] Field of Search .................................. 435/91.2, 91.1, 435/6; 536/24.3

[56] References Cited

PUBLICATIONS

Bellón, T., et al., "Identification and Expression of Two Forms of the Human Transforming Growth Factor–β–binding Protein Endoglin with Distinct Cytoplasmic Regions", 1993, *Eur. J. Immunol.*, 23:2340–45.

Braverman, I., et al., "Ultrastructure and Three-Dimensional Organization of the Telangiectases of Hereditary Hemorrhagic Telangiectasia", 1990, *J. Investigative Dermatology*, 95:422–27.

Cheifetz, S., et al., Endoglin Is a Component of the Transforming Growth Factor–β Receptor System in Human Endothelial Cells, 1992, *J. Biological Chem.*, 267:19027–30.

Dumont, D., et al., "Dominant–negative and Targeted Null Mutations in the Endothelial Receptor Tyrosine Kinase, tek, Reveal a Critical Role in Vasculogenesis of the Embryo", 1994, *Genes & Develop.*, 8:1897–909.

Fernández–Ruiz E., et al., "Assignment of the Human Endoglin Gene (END) to 9q34→qter", 1993, *Cytogenet. Cell Genet.*, 64:204–207.

Franzén, P., et al., "Cloning of a TGFβ Type I Receptor That Forms a Heteromeric Complex with the TGFβ Type II Receptor", 1993, *Cell*, 75:681–92.

Gougos, A., et al., "Primary Structure of Endoglin, and RGD–containing Glycoprotein of Human Endothelial Cells", 1990, *J. Biol. Chem.*, 265:8361–64.

Gougos, A., et al., "Identification of Distinct Epitopes of Endoglin, and RGD–containing Glycoprotein of Endothelial Cells, Leukemic Cells, and Syncytiotrophoblasts", 1992, *Int'l Immunology*, 4:83–92.

Hashimoto, K., et al., "Hereditary Hemorrhagic Telangiectasia", 1972, *Oral Surg.*, 34:751–67.

Jahnke, V., "Ultrastructure of Hereditary Telangiectasia", 1970, *Arch. Otolaryng.*, 91:262–65.

Jennings, J., et al., "Comparison of the Biological Actions of TGF Beta–1 and TGF Beta–2: Differential Activity in Endothelial Cells", 1988, *J. Cellular Physiol.*, 137:167–72.

Lastres, P., et al., "Regulated Expression on Human Macrophages of Endoglin, an Arg–Gly–Asp–containing Surface Antigen", 1992, *Eur. J. Immunol.*, 22:393–97.

(List continued on next page.)

*Primary Examiner*—Kenneth R. Horlick
*Assistant Examiner*—Joyce Tung
*Attorney, Agent, or Firm*—Fish & Richardson P.C.

[57] ABSTRACT

A method of diagnosing hereditary haemorrhagic telangiectasia (HHT) which includes the steps of:
  obtaining a sample of genomic DNA from a patient or fetus; and
  determining whether the DNA contains a mutation in a gene encoding endoglin, betaglycan, TGF-β type I receptor (RI), TGF-β type II receptor (RII), or TGF-β/activin type I receptor (TSR-I), such a mutation being an indication that the patient or fetus bears a gene making the patient or fetus susceptible to HHT.

12 Claims, 16 Drawing Sheets

OTHER PUBLICATIONS

López–Casillas, F., et al, "Structure and Expression of the Membrane Proteoglycan Betaglycan, a Component of the TGF–β Receptor System", 1991, *Cell,* 67:785–95.

López–Casillas, F., et al, Betaglycan Presents Ligand to the TGFβ Signaling Receptor, 1993, *Cell,* 73:1435–44.

Luscinskas, F., et al., "Integrins as Dynamic Regulators of Vascular Function", 1994, *FASEB J.,* 8:929–38.

Madri, J., et al., "Interactions of Vascular Cells with Transforming Growth Factors–$\beta^{\alpha}$", 1990, *Annals of NY Acad Sciences,* 593:243–58.

Menefee, M., et al., "Hereditary Hemorrhagic Telangiectasia (Osler–Weber–Rendu Disease)", 1975, *Arch. Otolaryngol.,* 101:246–51.

Mathew, S., et al., "Transforming Growth Factor Receptor Gene TGFBR2 Maps to Human Chromosome Band 3p22", 1994, *Genomics,* 20:114–15.

Millauer, B., et al., "High Affinity VEGF Binding and Developmental Expression Suggest Flk–1 as a Major Regulator of Vasculogenesis and Angiogenesis", 1993, *Cell,* 72:835–46.

Morén, A., et al., "Molecular Cloning and Characterization of the Human and Porcine Transforming Growth Factor–β Type III Receptors", 1992, *Biochem. and Biophys. Res. Commun.,* 189:356–62.

Schnürch, H., et al., "Expression of tie–2, a Member of a Novel Family of Receptor Tyrosine Kinases, in the Endothelial Cell Lineage", 1993, *Development,* 119:957–68.

Shovlin, C., et al., "A Gene for Hereditary Haemorrhagic Telangiectasia Maps to Chromosome 9q3", 1994, *Nature Genetics,* 6:205–209.

St.–Jacques, S., et al,. "Molecular Characterization and in Situ Localization of Murine Endoglin Reveal that is a Transforming Growth Factor–β Binding Protein of Endothelial and Stromal Cells", 1994, *Endocrinology,* 134:2645–57.

Wang, X., et al., "Expression Cloning and Characterization of the TGF–β Type III Receptor", 1991, *Cell,* 67:797–805.

White, M., et al., "Detecting Single Base Substitutions as Heteroduplex Polymorphisms", 1992, *Genomics,* 12:301–306.

Wrana, J., et al., "TGFβ Signals Through a Heteromeric Protein Kinase Receptor Complex", 1992, *Cell,* 71:1003–14.

Wrana, J., et al., "Mechanism of Activation of the TGF–β Receptor", 1994, *Nature,* 370:341–47.

Attisano et al., "Identification of Human Activin and TGFβ Type I Receptors That Form Heteromeric Kinase Complexes with Type II Receptors", 1993, *Cell* 75:671–680.

Heutink et al., "Linkage of hereditary haemorrhagic telangiectasia to chromosome 9q34 and evidence for locus heterogeneity", 1994, *J. Med. Genet.,* 31:933–936.

Lin et al., "Expression Cloning of the TGF–β Type II Receptor, a Functional Transmembrane Serine/Threonine Kinase", 1992, *Cell* 68:775–785.

McAllister et al., "Genetic heterogeneity in hereditary haemorrhagic telangiectasia: possible correlation with clinical phenotype", 1994, *J. Med. Genet.,* 31:927–932.

McDonald et al., "A disease locus for hereditary haemorrhagic telangiectasia maps to chromosome 9q33–34", 1994, *Nature Genetics,* 6:197–204.

Porteous et al., "Genetic heterogeneity in hereditary haemorrhagic telangiectasia", 1994, *J. Med. Genet.,* 31:925–926.

Yamashita et al., "Endoglin Forms of Heteromeric Complex with the Signaling Receptors for Transforming Growth Factor–β", 1994, *J. Biol. Chem.,* 269:1995–2001.

Ge et al. "Cloning and expression of a cDNA encoding mouse endoglin, an endothelial cell TGF–β Ligand", 1994, *Gene,* 138:201–206.

McAllister et al., "Endoglin, a TGF–β binding protein of endothelia cells, is the gene for hereditary haemorrhagic telangiectasia type 1", 1994, *Nature Genetics,* 8:345–351.

O'Connell et al., "Endoglin: a 180–kD endothelial cell and macrophage restricted differentiation molecule", 1992, *Clin. exp. Immunol.,* 90:154–159.

Exon 1

```
 1    ATGGACCGCGGCACGCTCCCCTCTGGCTGTTGCCCTGCTGCTGGCCAGCTGCAGCCTTCAGCCCCACAAGTCTTGCAGAAACAGTCCATTGT
 1    MetAspArgGlyThrLeuProLeuAlaValAlaLeuLeuLeuAlaSerCysSerLeuSerProThrSerLeuAlaGluThrValHisCys
```

Exon 2

```
 91   GACCTTCAGCCTGTGGGCCCCTGAGAGGGGCGAGGTGACATATACCACCAGTGTCCAGTTCTCGAAGGGTCTGGCTGCAGGCCCCAATGCC
 31   AspLeuGlnProValGlyProGluArgGlyGluValThrTyrThrThrSerValGlnValSerLysGlyCysValAlaGlnAlaProAsnAla

181  ATCCTTGAAGTCCATGTCCTCTTCCTGGAGTTCCCAACGGGCCCGTCACAGGCCCCAGGCATCCAAGCAAAATGCACC
 61   IleLeuGluValHisValLeuPheLeuGluPheProThrGlyProSerGlnAlaSerLysGlnAsnGlyThr
```

Exon 3

```
 271  TGGCCCCCAGAGAGTGCTTCTGGTCCTCAGTGTAAACAGTGTCTTCCTGCATTCCAGGCCCTGGAATCCCACTGCCACTTGGCCTAC
 91   TrpProProGluSerAlaSerGlyProGlnCysLysGlnCysLeuProAlaPheGlnAlaLeuGluSerHisCysHisLeuAlaTyr

361  AATTCCAGCCTGGTCACCTTCCAAGAGCCCCCGGGGGTCAACACCAGAGCTGCCATCCTCCCCAAGACCCAGATCCTTGAGTGGCA
 121  AsnSerSerLeuValThrPheGlnGluProProGlyValAsnThrArgAlaAlaIleLeuProLysThrGlnIleLeuGluTrpAla
```

Exon 4

```
 451  GCTGAGAGGGCCCCATCACCTCTGCTGAGTGAATGACCCCAGAGACATCCTCCTCCGACTGGGCAAGCCCAGGGTCACTGTCC
 151  AlaGluArgGlyProIleThrSerAlaAlaGluLeuAsnAspProGlnSerIleLeuLeuArgLeuGlyLysProArgValThrVal

541  TTTCTGCATGCTGGAAGCCAGCCAGGACATGGGCCGCACGCTCGAGTGGCGCGGCGGCTACTCCAGCTTGGTCCGGGCTGCCACTTGGAA
 181  PheCysMetLeuGluAlaSerGlnAspMetGlyArgThrLeuGluTrpArgArgGlyArgThrProAlaLeuValArgGlyCysHisLeu
```

Exon 5

```
 631  GGGCGTGGCCGGCCACAAGGAGGCGCACATCCTGAGGGTCCTGCCCGGCCACTCGGCCGGCCCCCGACGGTGAAGGTGAACTG
 211  GlyValAlaGlyHisLysGluAlaHisIleLeuArgValLeuProGlyHisSerAlaGlyProArgThrValThrValLysValGluLeu
```

FIG. 1A

```
                    Exon 6
721   AGCTGCGCACCCGGGATCTCGATGCCGTCCTCCTCATCCTGCAGGTCCCCCCTACGTGTCCTGGCTGTCCTCATCGACGCCAACCACACATGCAG
241   SerCysAlaProGlyAspLeuAspAlaValLeuIleLeuGlnGlyProProTyrValSerTrpLeuIleAspAlaAsnHisAsnMetGln
                  ▽         *
811   ATCTGGACCACTGGAGAATACTCCTTCAAGATCTTTCCAGAGAAAACATTCGTGGCTTCAAGCTCCCAGACACACTTCAAGGCTCCTG
271   IleTrpThrThrGlyGluTyrSerPheLysIlePheProGluLysIleArgGlyPheLysLeuProAspThrProGlnGlyLeuLeu
                                                         Exon 7
901   GGGGAGGCCCGATGCTCAATGCCAGCATTGTGGCATCCTTCGTGGAGCTACCGCTGGCCAGCATTGTCTCACTTCATGCCTCCAGCTGC
301   GlyGluAlaArgMetLeuAsnAlaSerIleValAlaSerPheValGluLeuProLeuAlaSerIleValSerLeuHisAlaSerSerCys
                                                                                    Exon 8
991   GGTGGTAGGCTGCAGACCTCACCCGCACCAGATCCAGACCCTGGTACTAAAGAAAGAGCTTGTTGCGCATTGAAGTGCACCATCACGGGCCTGACCTTCTGG
331   GlyGlyArgLeuGlnThrSerProAlaProIleGlnThrProLysAspThrCysSerProGluLeuMetSerLeuIleGln
            ▽                                                                                    ▽
1081  ACAAAGTGTGCCGACGACCGCATGACCCTGGTACTAAAGAAAGAGCTTGTTGCGCATTGAAGTGCACCATCACGGGCCTGACCTTCTGG
361   ThrLysCysAlaAspAspArgMetThrLeuValLeuLysLysGluLeuValAlaHisLeuLysLysCysThrIleThrGlyLeuThrPheTrp
                                                      Exon 9
1171  GACCCCAGCTGTGAGGCAGAGGACAGGGGTGACAAGTTTGTCTTGCCAGTGCAGTGTCAGAAGTATG
391   AspProSerCysGluAlaGluAspArgGlyAspLysPheValLeuArgSerAlaTyrSerSerCysGlyMetGlnValSerAlaSerMet
            ▽
1261  ATCAGCAATGAGGCGGTGGTCAATATCCTGTCGAGCTCAATCACCACCAGCGGGAAAAAGGTGCACTGCCTCAACATGGACAGCCTCTCTTTC
421   IleSerAsnGluAlaValValAsnIleLeuSerSerSerProGlnArgLysLysValHisCysLeuAsnMetAspSerLeuSerPhe
```

FIG. 1B

```
             Exon 10                                                          ▽
1351  CAGCTGGGCCTCTACCTGCTCCAGCCCCACACTTCCTCCAGGCCTCCAACACCATGAGCCGGGGCAGCAGAGAGCTTTGTGCAGGTCAGAGTGTCC
 451  GlnLeuGlyLeuTyrLeuSerProHisPheLeuGlnAlaSerAsnThrIleGluProGlyGlnGlnSerPheValGlnSerPheValArgValSer 1441  CCATCCGTCTCCGAGTTCCTGCTCCAGTTAGACAGCTGCCACTTGGGACTTGGGCCTGAGGGAGGCACCTGGAACTCATCCAGGCCGG
 481  ProSerValSerGluPheLeuLeuGlnLeuAspSerCysHisLeuGlyLeuGlyProGluGlyGlyThrValGluLeuIleGlnGlyArg Exon 11
1531  GCGGCCAAGGGCAACTGTGTGAGCCTGCTGTCCCCAAGCCCCGAGGGTGACCCGCGCTTCAGCTTCCTCCACTTCTACACAGTACCC
 511  AlaAlaLysGlyAsnCysValSerLeuLeuSerProSerProGluGlyAspProArgPheSerPheLeuHisPheTyrThrValPro 1621  ATACCCAAAAACCGGCACCCTCAGCTGCACGGTAGCCCTGCTCCAAGACCGGTCTCAAGACAAGGAAGTCCATAGGACTGTCTTCATG
 541  IleProLysThrGlyThrLeuSerCysThrValAlaLeuArgProLysThrGlySerGlnAspProLysThrValPheMet Exon 12                                                          Exon 13
1711  CGCTTGAACATCATCAGCCCTGACCTGTCTGGTTGCACAAGCAAAGGCCTCGTCCTGCCCGCCGTGCATCACCTTTGGTGCCTTC
 571  ArgLeuAsnIleIleSerProAspLeuSerGlyCysThrSerLysGlyLeuValLeuProAlaValLeuGlyLeuIleThrPheGlyAlaPhe ▽
1801  CTCATCGGGGCCCTGCTCACTGCTGCACATCTACTCGACACTCGTTCCCCCAGCAAGGGGAGCCCGTGGTGGCGGTGGCT
 601  LeuIleGlyAlaLeuLeuThrAlaAlaAlaLeuTrpTyrIleTyrSerHisThrArgSerProSerLysArgGluProValValAlaValAlaAla Exon 14
1891  GCCCCGGCCTCCTCGGAGAGCAGCAGCACCAACCACAGCATCGGAGCACTGGTGTGAACTCACCCTGGAGCCAGTCCTCCACT
 631  AlaProAlaSerSerGluSerSerSerThrAsnHisSerIleGlySerThrGlnSerThrProCysSerThrSerMetAla***

CGGCCCCCCGGCCCTGCGCCAGCAGAGAGCAGCAGCCGCCAGCTGGGAGCACTGGTGTGAACTCACCCTGGAGCCAGTCCTCCACT
      CGACCCAGAATGGAGCCCTGCTCTCCCGCTCTCCCGCCTCCCGGCTCCCTCTCAGAGGCCTGCAGCCACTGGCTGCAGCCACTGGCTGCAGCACC
      TTGGGGTCCCTCCACCACCCCAGTGGGTCTGGGATATGGCTGCCCAGGAGACAGACCACTTGCCACGCTGTTGTAAA
      AACCCAAGTCCCTGTCATTTGAACCTGGATC
```

FIG. 1C

```
              820
               |
Normal     ACT GGA GAA TAC TCC TTC AAG
           Thr Gly Glu Tyr Ser Phe Lys Mutant     ACT GGA GAA TAG TCC TTC AAG
           Thr Gly Glu ***
```

```
       874
        |
NORMAL  CTC CCA GAC ACA CCT CAA GGC CTC CTG GGG GAG GCC CGG ATG CTC AAT GCC AGC ATT
        Leu Pro Asp Thr Pro Gln Gly Leu Leu Gly Glu Ala Arg Met Leu Asn Ala Ser Ile

MUTANT                                                      CTC CCA GAT GCC AGC ATT
                                                            Leu Pro Asp Ala Ser Ile
```

FIG. 4C

```
       1543
        |
NORMAL  AAC TGT GTG AGC CTG CTG TCC CCA AGC CCC GAG GGT GAC
        Asn Cys Val Ser Leu Leu Ser Pro Ser Pro Glu Gly Asp

MUTANT  AAC TGT GTG ACT GCT GTC CCC AAG CCC CGA GGG TGA
        Asn Cys Val Thr Ala Val Pro Lys Pro Arg Gly ***
```

Exon 1

ATGGACCGGCGGCACGCTCCCTTGCCTTGCTGCCTGCTGCTGCTGCCAGCTGCAGCCTCAGCCCCACAA-----aatccatgaacgaatataatgatat p27 for
cacctcataaggtggctgtgatgcaggaaagcngttagctcatgtcaagtcccctaggagacgttggaaagtaggagtcattgtcatcacctatc tcacctgcctcttttcatgtcaagtcccctaggagacgtttggaaagtaggagtcattgtcatcacctattctcacctgcctcttttccgatgttctc

Exon 2 caacagGTCTCTGCAGAAACAGTCCATTGTGACCTTCAGCCTGTGGGCCCCGAGAGGGCGAGGTGACATATACCACTAGCCAGTCTCGAAGGGCTGCGT GGCTCAGGGCCCCAATGCCATCCTTGAAGTCCATGTCCTTCTCTTCCTGAGTTCCAAACGgtgagtgtccatggcaggtcggtgggggctcagaggaag p27 rev
ctccaagccagatgggtgaggggtgccttccttgtggctgtccctgggcagtggtcctgttagccccctgccaagagagtgatgtgggcatc

Exon 3 tcacagggcccataagaggtggcatttcta-----CGGCCCCGTCACAGCTGGAGCTGACTCTCCAGGCATCCAAGCAAAATGGCACCTGCCCCGAGAG GTGCTTCTGGTCTCAGTGTAAACAGCAGTGTCTTCCTGCATCCTGGAATCCACTTGCACTTGCCTAC------ggcctcttttctctcagcca p322 for
atgggctgactccacaaattacttcctgacctctacatggatagagagagggcacagggcaggaacagcgtgctgagcctccacatgtctcccagAATTC

Exon 4

CAGCCTGGTCACCTTCCAAGAGCCCCGGGTCAACACCAGAGCTGCATCCTTCCCAAGACCCTTGAGTGGGCAGCTGAGAGGGCCCAT

FIG. 5A

CACCTCTGCTGCTGAGCTGAATGACCCCCAGAGCATCTCCTCCGACTGGGCCAAGgtcagtttcccagcaacctctctggcctcatgatactgctcag gaggaatctgagctcctctgcccacacctcaaacttgggcaccaagagtgcaggaggggacacgctgtgccacagttcacatgccacaagccagtgctgc p322 rev cttgggacagtgatggctcctccaccaaatatcagattgaagcatgtgaatatgccaggttctgacctaaa------ttggcaggtagtggtggaaggcaa p486 for gttcgaacctaggtcctcctgagcctctccctctgcagcaccgtcctgccccaccactatctttgctgtgggtgagggggtctgttagg tca Exon 5 gggctgctga------CCCAGGGGTCACTGTCGTCTTCTGCATGCTGGAAGCCAGCAGGACATGGGCCACGCTGAGTGGCGGCCGGTACTCCAGCCTTG p486 rev GTCCGGGGCTGCCACTTGAAGGCGTGGCCGGCCACAAGGAGGCGCACATCCTGAGGTCCCGGCGTCCTGCCGGCCACTCGGCCGCGgtatgctctcgccccgcccc tgacactagtcccccaccccgagagaccaccccctgaccccccccctctccgtccttataagcccacccagtccagaccccagcccccgcc p650 for gcagccctgtgagagcacagtcgctttctctactctaggctacgcccccttccctttgggcacaagctgccccagtccatcctatc ccataaaacccaacacctggccaggtaagagtgcagccgggccggcctgctccccgcctgctccccgcctcattgttccatcctgt p650 rev ctccccgcagGCCCCGACGGTGACGGTGAAGGTGAACTGAGCTGGCACTGAGGATCTGATGCCGTCCTCATCCTGCAGGGTCCCCCTACGTGCC Exon 6

TGGCTCATGAGCGCCAACACCACAACATGCAGATCTGGgtgagttgtgccgagctcccgggacacaaaccaaactcccaacctctggatcaggaagtttc

FIG. 5B

```
ctggaaggtgaaccccgagttgagctgaaggacaaatcacctatgccatacgtgagggaaggggccaggcaggagacgcagcaggagtggggacaca
         p778 for
gcaggaccgaggcctggcataacctggctgccctgctgtgtggcacagactgtgtccatgcccccctgttctgcctctctcccaccattagACCACTGGA Exon 7
GAATACTCCTTCAAGATCTTTCCAGAGAAAAACATTCGTGCCTTCAAGCTCCCAGACACACACCTTCAAGGCCTCCTGGGGAGGCCCGATGCTCAATGCCA GCATTGTGGCATCCTTCGTGGAGCTACCGCTGGCCAGCATTGTCTCACTTCATGCCTTCCAGCTGGGgtgagcaccctcccctgccctcctccttc
                                                 p778 rev
ccctcccttggatcagtggccacactgttggtgaagcaagtacatcagcctctctgagcctcattttctcatctgcac atgggaacaatggagtagctaatcatagaagagcctgagaatcgcttgaacctgggagatggaggttgcagtgagccaagatcgtgccactgccc
                                                                   pX8 for
agcccgggtaacagagcaaaactccgtctcaaaaaaaaaaaagcctggtgcggcacacatatcacacagtgaccagccgcctgcctg Exon 8
cctct-c-accccacaggtg------TGGTAGGCTGCAGACCTCACCGCACCACTCCTCCAAGGACACTTGTAGCCCGAGCTGCTCA TGTCCTTGATCCAGACAAAGTGTGCCGACGACGCCATGACCCTGTACTAAAGAAGAAGAGCTTGTTGCgtaagggaactcctgccctctggctcaggatg
         pX8 rev
acatggacatctggttcctccctagcccaagactcttggggtcctagcccaggcaggggggcaagtcacgtccctctgcaagccttagttttcccactt
```

FIG. 5C

```
gtataatggaattgataatgtacctaccacgtggtgagaattaaaggcagtctgacaggccaatcacgtggcacagtaagatgtggtacatagtaagtg cttagtaaatatgcagcactagtagtt------GCATTTGAAGTGCACCATCACGGGCCTGACCTTCTGGGACCCAGCTGTGAGGCAGAGGACAGGGG
                                                         Exon 9
TGACAAGTTTGTCTTGCGCAGTGCTTACTCCAGCTGTGCCATGCAGGTGTCAGCAAGGTGTGGTCAATGAGGCGGTGTCAATATCCTGTCGAGCTCA TCACCACAGCGG------gatcgcaccactgcactccagcctgggcgacagagcgagactccgtctcaaaaaaaaaaagagagtcaggcaactccac
                                                                                   p1274 for
agggccatgatgcctgttcctccccacaccccctgcgctggcgccgccagattgaccaagtctcctcccagAAAAGTGCAC
                                                      Exon 10
TGCCTCAACATGGACAGCCTCTCTTTCCAGCTGGGCCTTACCTCAGCGCCTCCACACTTCCTCCAACACCATGAGCGGGGCAGCAGAGCTTTG
                                                                                p1274 rev
TGCAGgtacctggcatgcctgtcaccct-----ttcctctaaccgaccttcttcccaccatgactccagagagatgagactcccagagtcaggagga gacagcctgggtgcacaggagagagaggagacagagaaggcattgctcaggacactgacaaggatgtggccctgtcctcctcctgcccagtacagg
                                                                 Exon 11
tccatgtctttctttccactgtgaggactcagggggtgggactctaattctagccgatatttgaaggcagcaggtggggtggggtgaagagcagctgcc
        p1391 for
catgccgngtggcctacctaccatgcagGTCAGAGTGTCCCCATCCGTCCGAGTTCCTGCTCCAGTTAGACAGCTGCCACCTGGACTTGGGGCCTG AGGGAGGCACCGTGAACTCATCAGGCCCGGGCGGCCCCAAGGCCAACTGTGTGAGCCGCCTGCTGTCCCCAAGCCCCAGCCCCGAGGGTGACCCCGGCTTCAGTTCCT
```

FIG. 5D

```
CCTCCACTTCTACACAGTACCCATACCCAAAACGGCACCTGCAGCCCTCAGCTGCCTGCGTCCCAGAGACCGGGTCTCAAGACCAGgtgagtggggcc tgggcggccagcttcaagtgggagcttccagtctgtgtttgcatgaaggacatggcagccacaggatgtggc cagctggtgaggg-----gatctttccaggactcaccagagcatccagctacgaagcggtggagatggattcaaagccaaggctctagggtgggct
             p1649 for
ggggtcacggagccaggagtaaacctggaagcccctcccaaaggtgccacatactgctctctcttttctcctccagGAAGTCCATAGGACTGTCTTCAT
Exon 12                                                                          p1649 rev
GCGCTTGAACATCATCAGCCCTGACCCTGTCTGtgagctccctccagtctccgggtttgttctagtgctgaggtcacagtagggcacagcgggcagc cctgagaacggcctggcacatagcacatggcaaggtggaNNNNNNNccctctaggtggacagtcctagcaaccatggctcaatnncaggcctgctgtga
                                                                                    p1702 for
tgagcccgtttgctgcagaggagactgaggttcagagaagtcgaggtccatggctcagcagagctggcaccaaaccacatgggccagcaacaggg taggggatggggcaggggcagagtggcagtgctgattggcgtggcctctctagGTTGCACAAGCAAAGGCCTGCTCGCCGCCGTGCTGGCATCAC
Exon 13
CTTTGGTGCCTTCCTCATCGGGGCCCTGCTCACTGCGTGCACTCTGGTACATCTACTCGCACACCGgtgagtacccacaggccccacagtgagcatgccgg
```

FIG. 5E

```
                       p1702 rev    p1815 for
gcccctccatccaccggggagcctctgaggattgagggccctgaggacccctgacctccgcctcccgctcccag Exon 14
GTTCCCCAGCAAGCGGAGCCCGTGTGGCTGCCTCCTCCGAGCAGCAGCACCAACCACAGCATCGGAGCACCCAGAGCACCCC p1815 rev
CTGCTCCACCAGCAGCATGGCATAGCCCggccccccgctcgccagcaggagagactgagcagccgccagctgggactggtgtgaactcaccct gggagccagtcctccactcgaccagaatggagcctgtctccgcctaccttccgcctcccctctcagaggcctgctgccagtgcagccactgctt ggaacaccttggggtccctccaccccacagaaccttcaaccagtgggtctgggatatggctgccaggagacagaccacttgccacgctgttgtaaaaa cccaagtccctgtcatttgaacctgatccagctggtgaactgactgagctgggcaggaagggagaacttgaaacagattcaggccagcccagccaa cagca  cctccccgctgggaagagaagagggccacctgatctatcctgcgcctccacacctgaacttgcctaactaactggcagg ggagacaggagcctagcggagcccagcctgggagccagagagtgcaagaacagtgggcgttgggagcctagctcctgccacatggagccccctctgcc ggtcggggcagcagcagagggggagtagccaagctgcttgtcctgggcctgccctgtgtattcaccaccaataatcagaccatgaaacctgaaaaaaa aaaaaa
```

FIG. 5F

DIAGNOSIS OF AND THERAPY FOR HEREDITARY HAEMORRHAGIC TELANGIECTASIA

This application is a continuation-in-part of U.S. Ser. No. 08/346,129.

The experimental work reported herein was sponsored in part by National Institutes of Health Grant No. 1 R01 HL 49171-01. The U.S. Government therefore has certain rights in the invention.

BACKGROUND OF THE INVENTION

The field of the invention is diagnosis and genetic therapy for inherited diseases.

Hereditary haemorrhagic telangiectasia (HHT) or Osler-Weber-Rendu disease (OMIM #18730) is an autosomal dominant disorder characterized by multisystemic vascular dysplasia and recurrent haemorrhage. The disorder is named after the recurrent hemorrhage from vascular lesions, especially in the nasal mucosa and gastrointestinal tract, and for the presence of mucosal, dermal and visceral telangiectases. Pulmonary arteriovenous malformations (PAVMs) occur in approximately 20% of patients and are associated with serious complications including stroke and brain abscess. Other neurological manifestations include cerebral arteriovenous malformation, aneurysm and migraine headache.

Ultrastructural analyses of the vascular dysplasia seen in affected individuals have failed to demonstrate a unique pathological abnormality that might suggest the nature of the primary biochemical defect. Studies indicate that the dilated channels of telangiectases are lined by a single layer of endothelium attached to a continuous basement membrane (Jahnke, Arch. Ototaryngol. 91:262–265, 1970; Hashimoto and Pritzker, Oral Surg., Oral Med., Oral Pathol. 34:751–768, 1972). The earliest event in the formation of telangiectases appears to be dilation of post-capillary venules (Braverman et al., J. Invest Dermatol. 95:422–427, 1990). Eventually the dilated venules connect to enlarging arterioles through capillary segments which later disappear, creating direct arteriolar-venular connections. This sequence of events is associated with a perivascular mononuclear infiltrate (Braverman et al., J. Invest Dermatol. 95:422–427, 1990). Various explanations have been put forward to explain the angiodysplasia seen in HHT, including endothelial cell degeneration (Manafee et al., Arch. Ototaryngol. 101:246–251, 1975), defects in endothelial junctions (Hashimoto and Pritzker, Oral Surg., Oral Med., Oral Pathol. 34:751–768, 1972), lack of elastic fibers and incomplete smooth muscle cell coating of the vessels (Jahnke, Arch. Otolaryngol. 91:262–265, 1970), and weak connective tissue surrounding the vessel (Manafee et al., Arch. Otolaryngol. 101:246–251, 1975).

Genetic linkage for some HHT families was recently established to markers on chromosome 9q33-q34 (McDonald et al., Nature Genet. 6:197–204, 1994; Shovlin et al., Nature Genet. 6:205–209, 1994) and the locus was named OWR1. Genetic heterogeneity was established with the identification of some families clearly not linked to this region (Shovlin et al., Nature Genet. 6:205–209, 1994). The identification of key obligate recombinants in affected individuals allowed refinement of the OWR1 locus and placed the most likely candidate interval between D9S60 and D9S61 in a 2 centiMorgan (cM) interval (Shovlin et al., Nature Genet. 6:205–209, 1994).

SUMMARY OF THE INVENTION

The present invention is based upon the discovery that various defects in the gene encoding endoglin, a transforming growth factor β (TGF-β) binding protein, are responsible for some cases of HHT. Endoglin is a homodimeric integral membrane glycoprotein expressed at high levels on human vascular endothelial cells of capillaries, arterioles and venules in all tissues examined (Gougos and Letarte, J. Biol. Chem. 265:8361–8364, 1990; and Bellon et al., Eur. J. Immunol. 23:2340–2345, 1993). The cDNA sequence of human endoglin (SEQ ID NO:1) is shown in FIG. 1. In the work discussed herein, the genomic DNA of human endoglin has been cloned, its exon/intron structure determined, and the characteristics of certain HHT-associated mutations ascertained.

Endoglin is the most abundant TGF-β binding protein on endothelial cells (Cheifetz et al., J. Biol. Chem. 267:19027–19030, 1992). In the presence of TGF-β ligand, endoglin can associate with the two TGF-β signaling receptors RI and RII (Yamashita et al., J. Biol. Chem. 269:1995–2001, 1994). TGF-β is the prototype of a family of at least 25 growth factors which regulate growth, differentiation, motility, tissue remodeling, wound repair and programmed cell death in many cell types (Massague et al., Trends Cell Biol. 4:172–178, 1994, herein incorporated by reference).

The invention features an isolated DNA comprising a human genomic DNA sequence encoding endoglin. The genomic DNA preferably includes a nucleotide sequence corresponding to any one or more of SEQ ID NOs:9–19 and 42, and more preferably has the sequence of FIG. 5 (SEQ ID NOs:9–19 and 42). By "isolated DNA" is meant a DNA that is not immediately contiguous with at least one of the two genes with which it is immediately contiguous (i.e., one at the 5' end and one at the 3' end) in the naturally-occurring human genome. The term thus encompasses, for example, a genomic DNA fragment produced by PCR or restriction endonuclease treatment, whether such fragment is incorporated into a vector, integrated into the genome of a cell (at a site other than the naturally-occurring site), or independent of any other DNA sequences. The DNA may be double-stranded or single-stranded, sense or antisense.

Also within the invention is a single-stranded oligonucleotide 14–50 nucleotides in length having a nucleotide sequence identical to that of a portion of a strand of a human endoglin gene, which portion is within an intron of the gene and preferably borders an adjacent exon. Such an oligonucleotide can be paired with a second single-stranded oligonucleotide also 14–50 nucleotides length which is identical to a fragment of the strand complementary to the first strand (i.e., where the first strand is the sense strand, the second strand would be the antisense strand, and vice versa), which fragment is within (a) a second intron, (b) the 5' untranslated region immediately adjacent to the translation start signal, or (c) the 3' untranslated region immediately adjacent to the termination signal of the gene. The pair of oligonucleotides could serve as PCR primers selected to prime the PCR amplification of a single exon of the gene, or up to three exons (with intervening introns).

Described herein is a diagnostic method useful for determining whether a patient or a fetus bears a gene that would make the patient or fetus susceptible to HHT. This method includes the steps of obtaining a sample of genomic DNA from the patient (e.g., in the form of a blood sample) or fetus (e.g., by amniocentesis or chorionic villi sampling), and determining whether the DNA contains a mutation in a gene encoding endoglin, betaglycan, TGF-β type I receptor (RI), TGF-β type II receptor (RII), or TGF-β/activin type I receptor (TSR-I), such a mutation being an indication that the patient or fetus bears a gene making the patient or fetus susceptible to HHT. The method may include the step of treating the sample of genomic DNA with a restriction enzyme (e.g., MaeIII or BbvI where the gene of interest is endoglin). Alternatively or in addition, the method may include the step of subjecting the sample to PCR, using (1) a forward PCR primer complementary to a portion of the antisense strand of the gene, such portion being within (a) a first intron of said gene, or (b) the 5' untranslated region adjacent to the start codon of the gene; and (2) a reverse PCR primer complementary to a fragment of the sense strand of the gene, such fragment being within (a) a second intron of the gene, or (b) the 3' untranslated region adjacent to the termination codon of the gene.

Another diagnostic method of the invention includes the steps of identifying an individual suspected of being genetically predisposed to developing the HHT phenotype; obtaining from that individual a sample of mRNA from a tissue that normally expresses a gene of the TGF-β receptor complex, such as endoglin (e.g., cells of a newborn's placenta or umbilical cord or cells from the peripheral blood, vascular endothelium or mesenchyme of older individuals); subjecting the mRNA to RT-PCR to produce amplified cDNA having a sequence corresponding to that of a portion of the mRNA of the gene of interest; and determining whether the amplified cDNA includes a mutation responsible for the HHT phenotype, and thus indicates that the individual is genetically predisposed to developing the HHT phenotype.

The leukocyte antigen "CD 105" was assigned to endoglin at a recent Leukocyte typing workshop (Leukocyte Typing V, 1994). CD105/endoglin is expressed by cells within the "buffy coat" of peripheral blood. The "buffy coat" consists of leukocytes that are isolated by density centrifugation of whole blood. When mRNA is isolated from these cells, reverse transcribed, and amplified by a single round (35 cycles) of PCR, endoglin cDNA is reliably produced in quantities sufficient for mutational analysis by, for example, restriction digest. Unlike the umbilical cord or placenta, cells within peripheral blood provide a readily available source of endoglin mRNA.

The invention also includes compositions and methods for treating or preventing the symptoms of HHT by means of genetic therapy. Such methods would include identifying a patient who has inherited a defective gene that encodes a component of the TGF-β receptor complex (e.g., endoglin), and introducing an isolated DNA that encodes that component into the patient's cells. The targeted cells could include any of those that normally express genes in the TGF-β receptor complex, such as vascular endothelial cells, macrophages, or mesenchymal cells, and the DNA could be expressed by operably linking the cDNA or genomic DNA to a regulatory sequence that would direct expression in the targeted cells. The isolated DNA is preferably within (a) a vector suitable for introducing DNA into cells that would normally express endoglin, or (b) liposomes suitable for introducing DNA into these cells. The vector can include the endoglin cDNA sequence of SEQ ID NO:1 or a degenerate variant thereof, and may be introduced into the patient by intravenous or intra-arterial injection or by intravenous or intra-arterial catheter.

One could alternatively treat HHT by increasing the amount of TGF-β available at the cell surface. The object of this treatment would be to overcome the resistance of TGF-β-responsive cells caused by a malfunctioning TGF-β receptor complex. This could be accomplished by applying a pharmaceutical preparation containing TGF-β (preferably β1 or β3) to the skin or mucous membrane at the site of a telangiectasis (e.g., to the membranes lining the patient's nose), or by injection.

The invention further encompasses an animal model for HHT, such as a non-human transgenic animal (e.g., a rodent such as a mouse or rat) bearing a transgene encoding a truncated or otherwise mutant form of endoglin; a mouse, each of the cells of which has only one allele encoding wildtype endoglin; or a mouse which has no allele encoding wildtype endoglin.

Other features and advantages of the invention will be apparent from the detailed description that follows, and from the claims.

BRIEF DESCRIPTION OF THE DRAWINGS

FIG. 1 is a representation of the genomic structure of endoglin. The cDNA sequence of endoglin (SEQ ID NO:1) is shown with the deduced amino acid sequence (SEQ ID NO:2) below. The nucleotide and amino acid positions are based on numbering the A in the ATG start codon of the full-length L-form of endoglin (Bellon et al., Eur. J. Immunol. 23:2340–2345, 1993) as nucleotide number 1. Exons 1 through 14 are labelled above the cDNA sequence in bold and the intron/exon borders are marked with arrows. Exon 7 codes for amino acids 273–331; exon 11 spans residues 477–562. The four potential N-linked glycosylation sites are in boldface, italicized type and are underlined. The membrane spanning domain is double underlined. The positions of the mutations described in this report are shown in relation to the gene structure; the C to G change at nucleotide 831 is indicated by a star and the positions of the two deletions are underlined (nucleotides 882–920 and 1553–1554). The 2 bp deletion creates a premature termination codon, which is indicated by bold type.

FIG. 2c is a comparison of the normal (SEQ ID NO:3) and mutant (SEQ ID NO:4) DNA and amino acid sequences in the region of the mutation in sample 1159. This C to G substitution converts a tyrosine to a stop codon at amino acid 277.

FIG. 3a is a comparison of the normal (SEQ ID NO:5) and mutant (SEQ ID NO:6) DNA and amino acid sequences in the region of the deletion mutation in sample 8019 from the 9q3-linked Family 3186. This 39 bp deletion, which is located at nucleotide positions 882 through 920 in exon 7, removes 13 amino acids from the protein and alters the first amino acid (position 307) in a potential N-linked glycosylation site.

FIG. 4c is a representation of the normal (SEQ ID NO:7) and mutant (SEQ ID NO:8) DNA and amino acid sequences in the region of the 2 bp deletion in sample 2061. The two deleted nucleotides are underlined in the normal sequence. This mutation causes a frameshift and a premature termination after an additional seven amino acids.

FIG. 5 is a representation of a partial genomic DNA sequence of the wildtype human endoglin gene (SEQ ID NOs:9–19 and 42). Capital letters indicate coding sequence (exons), while lower-case letters indicate introns. Dashes indicate portions of the introns for which the nucleotide sequence has not yet been determined.

DETAILED DESCRIPTION

The endoglin gene previously was mapped to human chromosome 9q34 using fluorescence in situ hybridization (FISH; Fernandez-Ruiz et al., Cytogenet. Cell Genet. 64:204–207, 1993).

Genomic structure of endoglin

As an initial screen for gross abnormalities in the endoglin gene in affected HHT individuals, Southern blots of DNA from the probands of 33 unrelated families having family members with HHT were probed with a nearly complete cDNA of endoglin, the clone 18A of Gougos and Letarte, supra. This analysis using three restriction endonucleases revealed no gross abnormalities of the endoglin gene in these samples. Reverse transcription-PCR (RT-PCR) was attempted using RNA prepared from several Epstein-Barr virus-transformed lymphoblast lines established from our patient cohort, but expression levels of endoglin appeared to be too low to allow routine amplification in a single round (35 cycles) of PCR. As the expression of endoglin is restricted to endothelial cells, activated monocytes (Lastres et al., Eur. J. Immunol. 22:393–397, 1992), syncytiotrophoblast (Gougos et al., Int'l. Immunol. 4:83–92, 1992), and certain stromal cells (St. Jacques et al., Endocrinology 134:2645–2657, 1994), screening for mutations within endoglin cDNA was not feasible. The genomic structure of endoglin was therefore studied.

A gridded cosmid chromosome 9 library was screened with the 18A cDNA probe, and 17 cosmids were obtained. Southern analysis of these clones in comparison with total genomic DNA revealed that one cosmid, 21c10, appeared to contain most of the gene. This cosmid was subcloned into a phagemid library which was screened for positive plaques with the 18A cDNA probe. Hybridizing clones were converted to plasmids and sequenced using vector primers flanking the cloning site to identify intron-exon borders.

Figure 7:
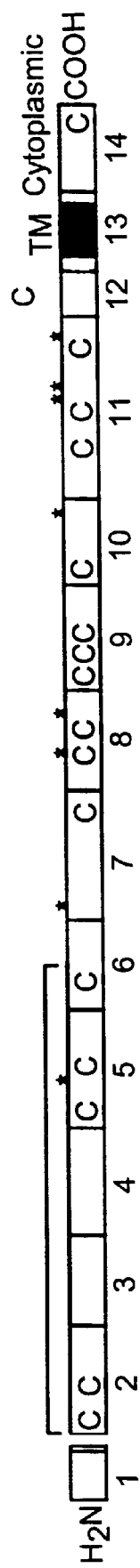
FIG. 7 is a schematic illustration of the endoglin protein, shown to scale with contributions from each exon shown by the boxes numbered below. Amino acid residues from the first of a portion of the second exon are cleaved from the mature protein and are shown separated from the main body of the protein. Exons 2–12 encode the extracellular domain, exon 13 encodes the transmembrane (TM) domain, and exon 14 encodes the cytoplasmic domain. The positions of the cysteine residues are marked with C. The approximate positions of truncation mutations, whether nonsense or frameshifts, are shown with the asterisks. The bracket delineates the betaglycan-related amino-terminal domain of endoglin, which may correspond to the TGF-β binding domain.

Preliminary sequence analysis suggests that the coding region of endoglin contains 14 exons (FIGS. 1 and 7). one or more splice junctions may remain unidentified within the 5' end of the gene, as the sequence denoted exon 1, which contains the putative signal peptide, was found to be missing in the 21c10 cosmid. There is also evidence for alternative splicing variants of the endoglin transcript. Since only one variant was used to identify subclones for genomic sequencing, it is possible that additional exons exist within the depicted coding region (FIG. 1). (The exon number assignments must be regarded as preliminary until the entire gene structure is resolved.)

The 14 exons are sufficiently small to allow for PCR amplification of each as a single unit (Table 1). The smallest is exon 12 which contains the complete membrane spanning domain and is 55 basepairs (bp) in length. The longest exon completely contained within the coding region is exon 11 (258 bp). Exon 14 contains at least 429 bp but contains only 125 bases of coding information, the remainder being the 3' untranslated region.

TABLE 1

PCR assays for endoglin exons

| Exon | Size (pb) | Forward Primer Sequence (5'->3') | Reverse Primer Sequence (5'->3') | PCR Prod. Size | Buffer | [MgCl2] | Annealing Temp | # of cycles |
|---|---|---|---|---|---|---|---|---|
| 1 | >67 | | | | | | | |
| 2 | 152 | cctcataaggtggctgtgatgatg SEQ ID NO: 20 | catctgccttggagcttcctct SEQ ID NO: 21 | 413 | BHB | 1.5 mM | 60° | 35 |
| 3 | 141 | | | | | | | |
| 4 | 163 | ttcctgacctcctacatgg SEQ ID NO: 22 | ctcttggtgcccaagttt SEQ ID NO: 23 | 330 | TNK 50 | 1.0 mM | 51° | 30 |

TABLE 1-continued

PCR assays for endoglin exons

| Exon | Size (pb) | Forward Primer Sequence (5'->3') | Reverse Primer Sequence (5'->3') | PCR Prod. Size | Buffer | [MgCl2] | Annealing Temp | # of cycles |
|---|---|---|---|---|---|---|---|---|
| 5 | 166 | cgggctctgttaggtgcag SEQ ID NO: 24 | gggtggggcttttataaggga SEQ ID NO: 25 | 294 | TNK 25 | 1.0 mM | 57° | 35 |
| 6 | 127 | ctgtccgcttcagtgttccatc SEQ ID NO: 26 | ggaaacttccctgatccagaggtt SEQ ID NO: 27 | 230 | TNK 100 | 1.5 mM | 59° | 40 |
| 7 | 176 | gaggcctggcataaccct SEQ ID NO: 28 | gtggccactgatccaagg SEQ ID NO: 29 | 315 | BMB | 1.5 mM | 60° | 35 |
| 8 | 141 | acacatatcacacagtgaccagc SEQ ID NO: 30 | ctaggggaggaaccagatgtc SEQ ID NO: 31 | | TNK 50 | 1.0 mM | 55° | 30 |
| 9 | 178 | | | | | | | |
| 10 | 117 | agattgaccaagtctccctccc SEQ ID NO: 32 | aggctgtctccctcctgactct SEQ ID NO: 33 | 227 | TNK 50 | 1.0 mM | 61° | 35 |
| 11 | 258 | actcaggggtgggaactctt SEQ ID NO: 34 | ccttccatgcaaaccacag SEQ ID NO: 35 | 430 | TNK 50 | 1.0 mM | 57° | 32 |
| 12 | 55 | gagtaaacctggaagccgc SEQ ID NO: 36 | gccactagaacaaacccgag SEQ ID NO: 37 | 164 | TNK 100 | 1.0 mM | 55° | 35 |
| 13 | 111 | ccagcacaacagggtaggggat SEQ ID NO: 38 | ctcagaggcttcactgggctcc SEQ ID NO: 39 | 255 | TNK 50 | 1.0 mM | 61° | 35 |
| 14 | >429 | tgaagcctctgagggattgagg SEQ ID NO: 40 | gagttcacaccagtgctcccag SEQ ID NO: 41 | 267 | TNK 50 | 1.0 mM | 57° | 40 |

Identification of HHT mutations

In an initial screen for mutations, primers located within the introns flanking exons 7 and 11 (the first exons to be identified) were designed to establish PCR assays for each exon (see Methodology). A panel of 68 DNA samples was used for the mutation screen. These were collected from probands of unrelated families, most of which were members of kindreds with PAVM involvement, increasing the likelihood that the individuals would harbour mutations at the OWR1 locus. The panel of DNA samples used in the initial mutation screen included affected individuals from nine families previously linked to 9q34 (McDonald et al., Nature Genet. 6:197–204, 1994; Porteous et al., J. Med. Genet. 31:925–926, 1994; McAllister et al., J. Med. Genet. 31:927–932, 1994; Heutink et al., J. Med. Genet. 31:933–936, 1994). Heteroduplex analysis was performed on amplified products from this cohort as a screen for potential mutations. Abnormal PCR products seen on these gels were directly sequenced for further analysis.

Figure 2A:
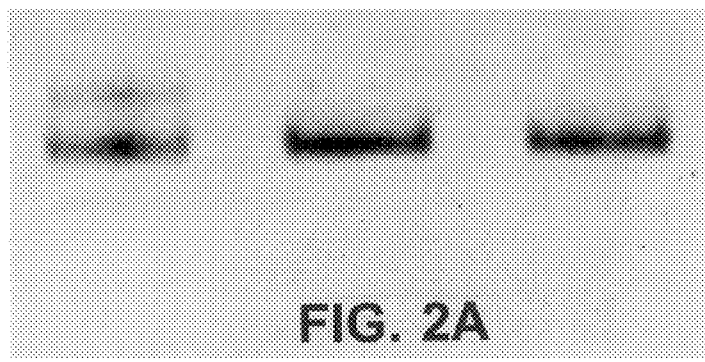
FIG. 2a is an heteroduplex analysis showing a shift in an affected proband (sample 1159; lane 1) next to two samples (lanes 2 and 3) not displaying this anomaly.
Figure 2B:
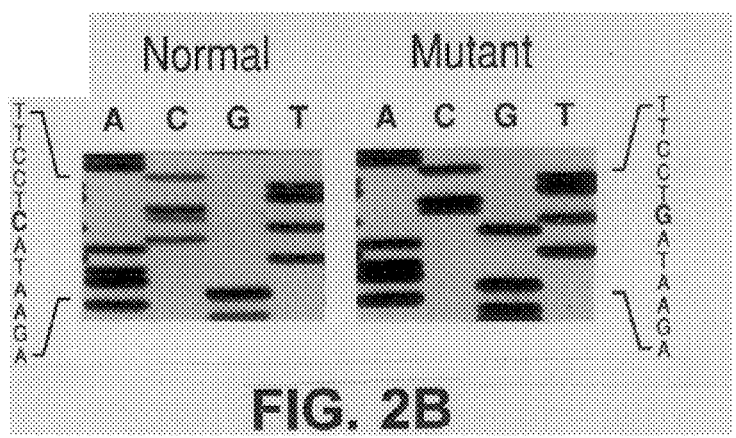
FIG. 2b is a photograph of a sequencing gel comparing the sequences of representative clones revealing the normal (C) and mutant sequence (G) of amplified exon 7 in sample 1159.

With the initial screen, three mutations in affected individuals were identified. The first mutation was identified by a heteroduplex shift in the exon 7 PCR product from sample 1159 (FIG. 2a). The products of two independent PCR reactions were directly sequenced, whereupon a C (normal) and a G (mutant) at nucleotide position 831 were clearly visible. PCR products amplified from this individual were then cloned and individual clones sequenced to validate the results of the direct sequencing (FIG. 2b). This change converts a tyrosine at codon 277 to a termination codon (FIG. 2c). This mutation is present in the proband of a pedigree with multiple affected members having documented PAVMs. However, additional members of this family were not available for analysis. The truncated protein resulting from this mutation would comprise only half of the extracellular domain and lack the membrane spanning and cytoplasmic domains.

Figure 3B:
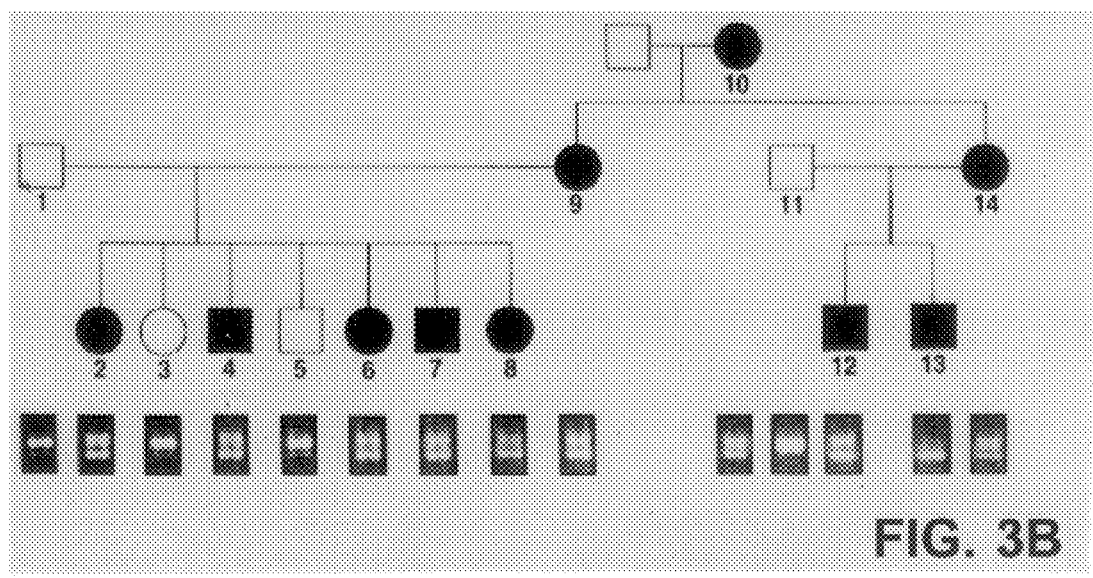
FIG. 3b is an illustration of the inheritance of HHT by the members of Family 3186, showing segregation of the 39 bp deletion. Agarose gel analysis of amplified exon 7 from each member of Family 3186 reveals the presence of a lower band (the 39 bp deletion product) in affected family members only. Preferential amplification of the smaller fragment is sometimes observed (see individual 13).

Amplification of exon 7 in sample 8019 revealed a second mutation, in a family (Family 3186) previously linked to 9q3. A second PCR fragment smaller than the wild-type fragment was visible in both agarose gels and heteroduplex analysis, suggesting the existence of a deletion. The smaller fragment was not seen in 278 normal chromosomes and is unlikely to be a polymorphism. Sequence analysis of the PCR products revealed a 39 bp deletion in the exon beginning at nucleotide position 882 of endoglin (FIG. 3a). This in-frame deletion removes 13 amino acids (amino acids 295 to 307) and alters the first amino acid of a potential N-linked glycosylation site (see FIG. 1). Amplification of this exon revealed the presence of the deletion in all affected family members, but no unaffected members (FIG. 3b).

Figure 4A:
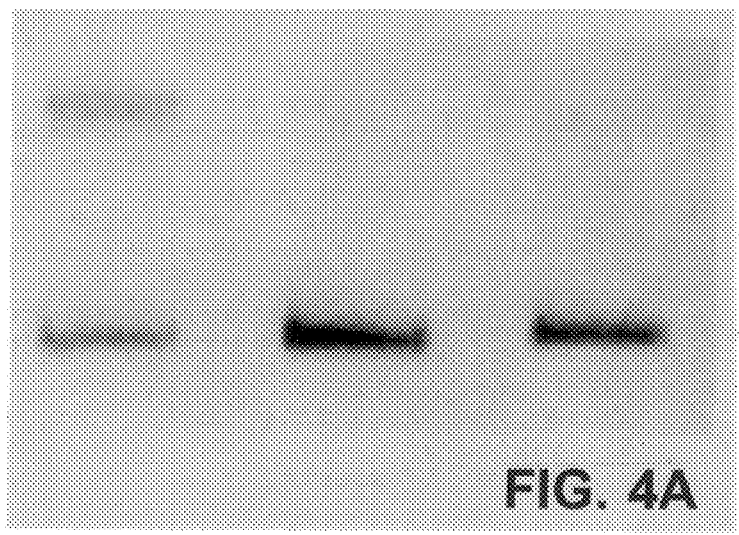
FIG. 4a is an heteroduplex analysis of sample 2061 showing a shift in an affected proband (sample 2061; lane 1) next to two samples (lanes 2 and 3) not displaying this anomaly.
Figure 4B:
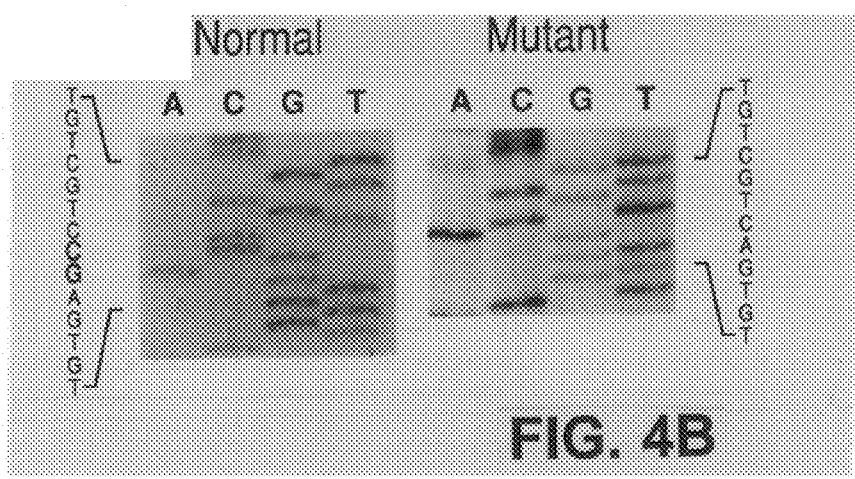
FIG. 4b is a photograph of gels indicating the sequence of the 2 bp deletion in sample 2061, compared to the normal sequence. The sequences of the two independently cloned PCR products of affected individual sample 2061 reveal the normal sequence and the 2 bp deletion in exon 11 beginning at nucleotide position 1553.
Figure 4D:
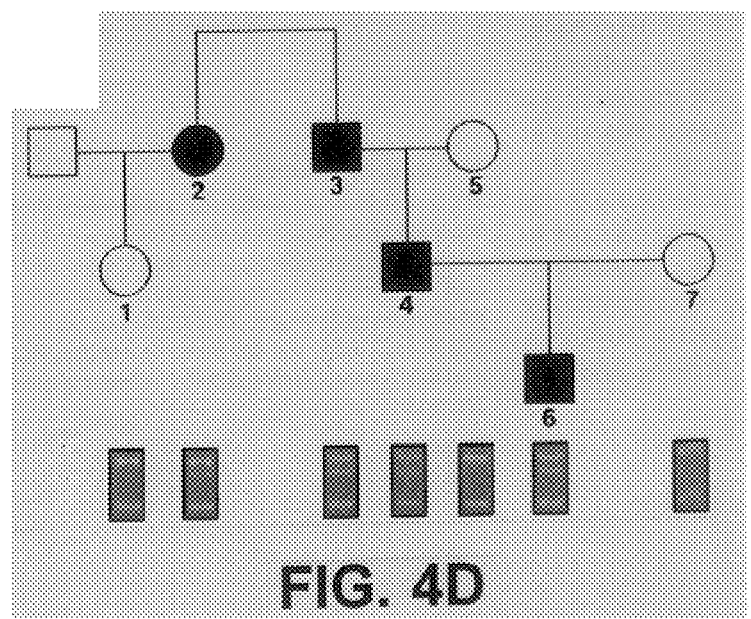
FIG. 4d is an illustration of the inheritance of HHT by the members of Family 63, and an agarose gel electrophoresis analysis of amplified exon 11 from each family member, showing segregation of the 2 bp deletion. The 2 bp deletion creates an additional MaeIII restriction site. Affected family members exhibit an additional novel fragment visible as the middle band in each lane, with half the intensity of the other two bands. A second novel band produced by digestion at this site is not visible on this gel.

Heteroduplex analysis of amplified exon 11 revealed a very pronounced band in sample 2061 that was not visible with agarose gel electrophoresis (FIG. 4a). Independent clones of the PCR product were sequenced, revealing the wild-type sequence and a 2 bp deletion beginning with nucleotide 1553 of endoglin (FIG. 4b). This deletion creates a MaeIII restriction site. This sample was from the proband of a family with multiple affected members displaying PAVMs. Exon 11 was amplified from all available family members and digested with MaeIII. All affected family members share the additional MaeIII site, whereas the unaffected members do not, establishing linkage of this mutation to the disease phenotype in this family (FIG. 4d). The mutation creates a frame shift that results in a premature termination codon 8 amino acids beyond the deletion (FIG. 4c). The predicted truncated protein would lack the membrane spanning and cytoplasmic domains of endoglin.

A subsequent screen detected six additional mutations. Primers were designed to amplify 11 of the 14 endoglin exons, heteroduplex analysis was performed, and PCR products were directly sequenced. Mutations were found in exons 5, 7, 8, 10 and 11, and all but one of these mutations would produce a truncated protein if translated. Each of the mutations was seen only in a single chromosome in over 160 total chromosomes analyzed. Where additional family members were available, the mutations were shown to co-segregate with the disease phenotype.

Figure 6A:
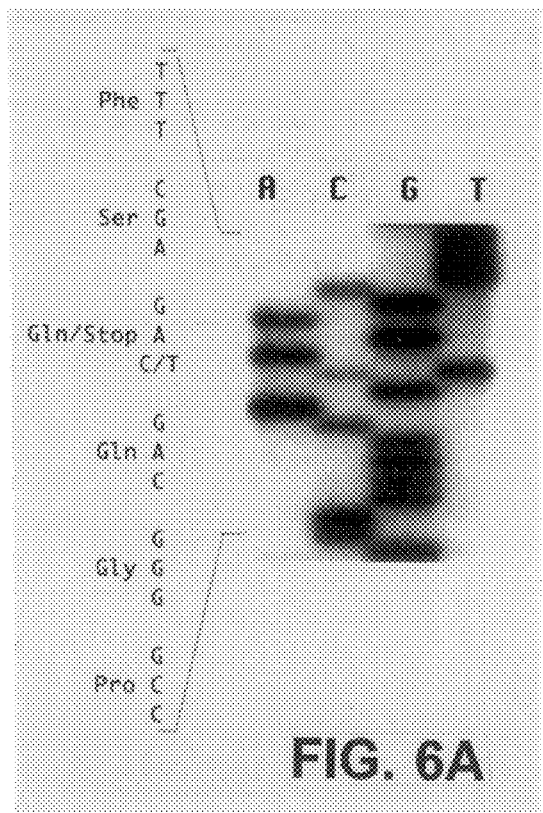
FIG. 6a is a photograph of a gel illustrating the sequence of an exon 10 mutation in sample 1247 of family 32. Direct sequencing reveals both the normal (C) and the mutant (T) at nucleotide 1414, which creates a premature termination at codon 472, CAG to TAG.
Figure 6C:
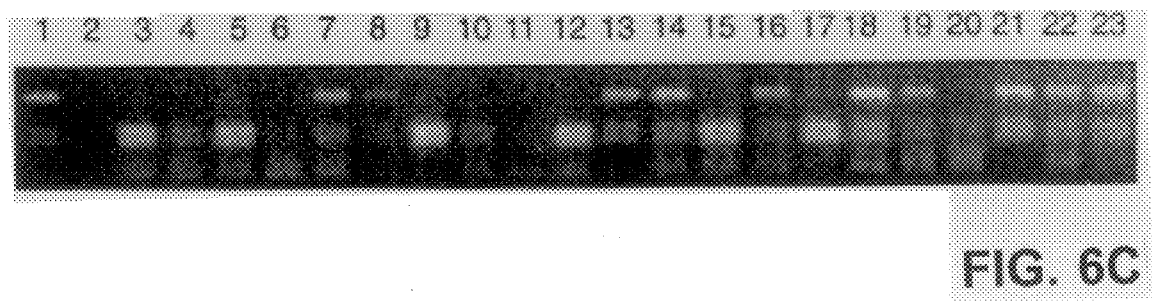
FIG. 6c is a photograph of a gel, each lane of which represents BbvI-digested DNA of amplified exon 10 from a member of family 32. This mutation removes a BbvI site in the amplification product. All unaffected members reveal the digested doublet bands, whereas all affected individuals show the presence of three bands, corresponding to the uncut (mutant) and cut (normal) fragments of exon 10.
Figure 6B:
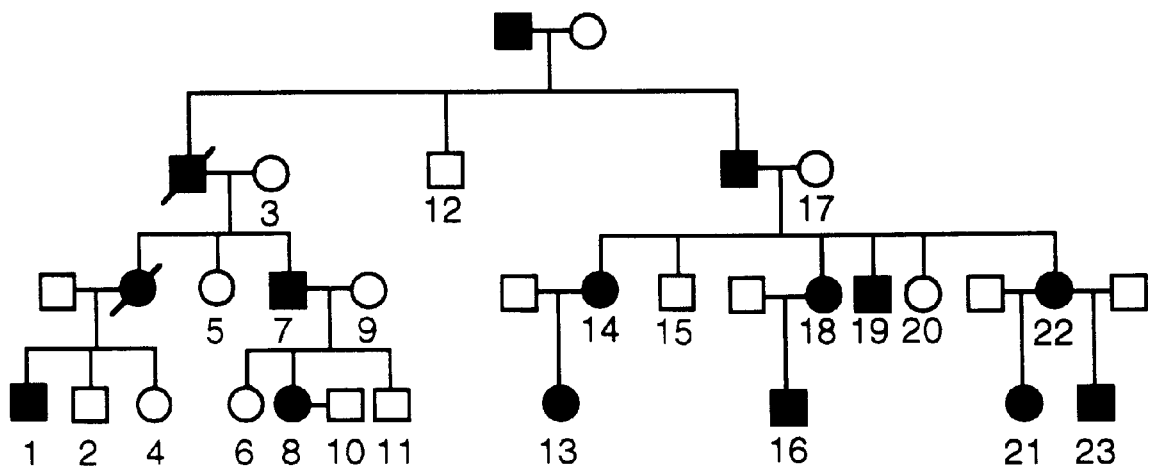
FIG. 6b is a representation of the pedigree of family 32 denoting affected (closed symbols) and unaffected (open symbols) individuals. The numbers beneath the symbols refer to lane position in FIG. 6c.

One of the mutations detected in the second screen includes a C to T base pair substitution, creating a stop codon in exon 10 in a previously described ORW1 family (McAllister et al., J. Med. Genet. 31:927–932, 1994). The normal and mutant bases were seen in direct sequencing of the PCR product (FIG. 6a). This point mutation removes a BbvI restriction site. Exon 10 was amplified from all available family members and digested with BbvI. All unaffected family members revealed the resulting digested fragments (normal allele), whereas all affected family members revealed the uncut fragment (mutant allele) in addition to the digested fragments (FIGS. 6b and 6c). A summary of all nine currently defined endoglin mutations appears in Table 2.

TABLE 2

Endoglin Mutation Summary

| Exon | Sample No. | Family No. | Type of Mutation |
|------|-----------|-----------|------------------|
| 5 | 1152 | | Substitution at position 587 creates stop condon TGG to TAG |
| 7 | 58019 | 3186 (5) | Deletion (39 bp) at position 882 (6) |
| 7 | 1159 | | Substitution at position 831, creates stop condon TAC to TAG (6) |
| 8 | 1275 | 56 (4) | Substitution at position 1050 creates stop condon TGT to TGA |
| 8 | 1160 | | Insertion (1 bp) at position 1111, frameshift creates premature stop condon |
| 10 | 1247 | 32 (4) | Substitution at position 1414, creates stop condon CAG to TAG |
| 11 | 102061 | | Deletion (2 bp) at position 1553, frameshift creates premature stop condon (6) |
| 11 | 1162 | | Deletion (1 bp) at position 1655, frameshift creates premature stop condon |
| 11 | 2241 | | Deletion (2 bp) at position 1550, frameshift creates premature stop condon |

DISCUSSION

These results, in which nine independent mutations in affected HHT individuals are identified, establish the endoglin gene as the HHT1 disease locus mapping to 9q3. The gene maps to the tightest HHT1 candidate interval on 9q33-q34, based on evidence from the mouse and human genetic and physical maps. The restricted tissue distribution of endoglin and its expression at high levels on the surface of endothelial cells is consistent with the pathology of the disorder.

One of the nine mutations described in this report would remove 13 amino acids from the extracellular domain of endoglin and could have a deleterious effect on receptor function. A defect in a cell surface TGF-β binding protein would account for the limited and localized nature of the vascular lesions present in this disease.

The eight remaining mutations create premature termination codons and would be expected to lead to reduced message levels that, if translated, would encode severely truncated proteins, suggestive of loss-of-function alleles. The apparent clustering of premature termination mutations in exons 5–11 is also consistent with a dominant-negative model. This model would suggest that the normal endoglin function is disrupted as a consequence of an effect caused by the mutant protein. Endoglin is isolated from cells as a homodimer that can be dissociated by reducing agents (Gougos and Letarte, J. Biol. Chem. 265:8361–8364, 1990; Gougos and Letarte, J. Immunol. 141:1934–1940, 1988). In affected individuals it is possible that normal/mutant heterodimers, which do not function properly or which lead to rapid turnover of the receptor complex, are assembled. Three cysteines are present in the processed endoglin protein prior to the first known truncation mutation in exon 5. One or more of these may be required for inter-molecular disulfide linkage, which might explain the apparent lack of truncation mutations prior to exon 5. Binding of TGF-β may also be required for the dominant-negative effect. Deletion of the amino-terminal endoglin-related domain of betaglycan abolishes the TGF-β binding activity of betaglycan (Lopez-Casillas et al., J. Cell Biol. 124:557–568, 1994). It is proposed that the corresponding region of endoglin constitutes the TGF-β binding domain of endoglin.

Alternatively, the mutant endoglin allele might produce a soluble polypeptide which can bind and sequester the TGF-β ligand. Deletion mutants of betaglycan which remove the transmembrane and cytoplasmic domains produce soluble polypeptides which can bind TGF-β and inhibit TGF-β binding to membrane receptors (Lopez-Casillas et al., J. Cell Biol. 124:557–568). In the same way, soluble endoglin may act as an antagonist of TGF-β signaling.

TGF-β in vivo is a potent angiogenic factor and a mediator of vascular remodelling as it controls extracellular matrix production by endothelial cells, smooth muscle cells and pericytes (Madri et al., *Endothelial cell dysfunctions* (eds. Simionescu & Simionescu) (Plenum Press, New York, 1992). Following soft tissue injury or in response to angiogenic factors, microvascular endothelial cells detach from their basement membrane, migrate and proliferate in the interstitial stroma, and form new microvessels. When grown in vitro in three-dimensional gels and in the presence of TGF-β, these endothelial cells form tube-like cellular aggregates with a lumen and tight junctions, and deposit an organized basement membrane, mimicking vessel formation (Madri et al., supra). However, TGF-β, almost exclusively in the β1 isoform, will inhibit the proliferation of endothelial cells grown on plastic (Madri et al., supra; Jennings et al., J. Cell Physiol. 137:167–172, 1988). The response of endothelial cells to TGF-β depends on the interaction with the surrounding extracellular matrix via integrins expressed on their surface (Luscinkas et al., FASEB J. 8:929–938, 1994). The production of matrix protein by stromal interstitial cells, smooth muscle cells, pericytes and endothelial cells and the expression of integrins on endothelial cells are also regulated by TGF-β (Madri et al., supra; Luscinkas et al., FASEB J. 8:929–938, 1994).

Endothelial cells lacking endoglin may respond poorly to TGF-β1 and thus form abnormal blood vessels, particularly in response to injury. TGF-β signalling is mediated by TGF-β receptors RI and RII, which form a heteromeric complex upon binding TGF-β (Wrana et al., Cell 71:1003–1014, 1992; Wrana et al., Nature 370:341–347, 1994). Endoglin, which binds TGF-β1 and -β3 with high affinity but does not bind TGF-β2 (Cheifetz et al., J. Biol. Chem. 267:19027–19030, 1992), is structurally related to betaglycan, which binds all three isoforms of TGF-β (Lopez-Casillas et al., Cell 67:785–795, 1991; Wang et al., Cell 67:797–805, 1991). Betaglycan in the presence of ligand interacts with the signaling kinase complex of RI and RII and potentiates the response to all three isoforms of the growth factor (Lopez-Casillas et al., Cell 73:1435–1444, 1993). Endoglin also interacts with the kinase complex, suggesting a potentiating role similar to that of betaglycan. Endothelial cells express very low levels of betaglycan, which may explain their poor response to TGF-β2 (Cheifetz et al., J. Biol. Chem. 265:20533–20538, 1990). Thus endoglin-deficient endothelial cells, as observed in HHT1-linked patients, would express only the signaling RI and RII complex and would lack the regulatory co-receptor capable of controlling the response. This might alter cell adhesion properties, leading to the vascular anomalies seen in this disorder. Stromal cells in several tissues (St. Jacques et al., Endocrinology 134:2645–2657, 1994) and activated monocytes (Lastres et al., Eur. J. Immunol. 22:393–397, 1992) also express endoglin and could be impaired in their response to TGF-β1 in the vascular lesions of HHT1 patients.

METHODOLOGY

Clinical evaluation. The diagnostic criteria used for collection of family members was as described (McDonald et al., Nature Genet. 6:197–204, 1994).

Genomic sequence determination. A nearly complete cDNA sequence of endoglin (18A) was used to screen a gridded chromosome 9 cosmid library (Los Alamos National Laboratory). One subclone that contained nearly all hybridizing bands that are seen with genomic DNA was subcloned using Lambda ZAP Express system (Stratagene). Plaque screens were performed by hybridization with the 18A cDNA probe to identify positive clones. Intron-exon borders were identified by sequencing these clones using the Sequenase Ver. 2.0 DNA sequencing kit (United States Biochemical) using both vector and exon primers.

PCR amplification on exons. Primers were designed from intron genomic sequences flanking exons 7 and 11 of endoglin. For exon 7 (nts 817–992), the forward primer is 5'-GAGGCCTGGCATAACCCT (SEQ ID NO:28), and the reverse primer is 5'-GTGGCCACTGATCCAAGG (SEQ ID NO:29). The 315 bp product was amplified using a buffer consisting of 10 mM Tris-HCl, pH 8.3; 1.5 mM $MgCl_2$; and 50 mM KCl. After initial denaturation, 35 cycles of the following program were run: 94° C. for 30 s; 60° C. for 60 s; 72° C. for 30 s. For exon 11 (nts 1429–1686), the forward primer is 5'ACTCAGGGGTGGGAACTCTT (SEQ ID NO:34) and the reverse is 5'-CCTTCCATGCAAACCA CAG (SEQ ID NO:35). The 430 bp product was amplified in 10 mM Tris-HCl, pH 8.3; 1 mM $MgCl_2$; 50 mM KCl; and 5 mM $NH_4Cl$. After initial denaturation, 32 cycles of the following program were run: 94° C. for 50 sec., 57° C. for 60 sec., 72° C. for 30 sec.

Each exon can be amplified using conditions described in Table 1. The amplification reaction contains 100 ng of genomic DNA, 100 ng of each oligonucleotide primer, 0.20 mM of each dNTP, and 1.25 U of Taq DNA polymerase in final volume of 25 μl. Reaction conditions were optimized individually for each primer pair by adjusting annealing temperatures and buffer conditions as described (Blanchard et al., PCR Meth. Applic. 2:234–240, 1993), using the Taq polymerase buffer supplied by Boehringer Mannheim Biochemicals, Indianapolis, Ind. (BMB).

Mutation analysis. Heteroduplex analysis was carried out as described using MDE gel mix (AT Biochem) with the addition of 15% urea. Samples were denatured for 5 min and allowed to slow cool before fragments were separated by electrophoresis on non-denaturing gels. Products were visualized by ethidium bromide staining. Altered PCR products detected by heteroduplex analysis were directly sequenced using AmpliTaq Cycle sequencing kit (Perkin Elmer). Primers were end-labelled and samples run on 6% polyacrylamide gels. PCR products of the individuals containing the identified stop codon and the 2 bp deletion were cloned into pCR-Script Direct SK(+) cloning vector using pCR-Script Direct SK(+) Directional Cloning Kit (Stratagene) and sequenced using Sequenase Ver. 2.0 (United State Biochemical).

EXAMPLE 1

Diagnosis

The discovery that a defect in a component of the TGF-β receptor complex underlies the HHT phenotype means that individuals (in particular, those with a family history of the disease) can be tested for inheritance of the disease gene even before symptoms appear. This will permit appropriate genetic counseling of those individuals who have inherited the disease. In addition, individuals diagnosed with the genetic defect can be closely monitored for the appearance of symptoms, permitting early intervention, including genetic therapy, as appropriate. Analysis can be carried out on any suitable genomic DNA sample from the individual to be tested. Typically, a blood sample from an adult or child, or a sample of placental or umbilical cord cells of a newborn would be used; alternatively, one could utilize a fetal sample obtained by amniocentesis or chorionic villi sampling.

It is expected that standard genetic diagnostic methods can be used. For example, PCR (polymerase chain reaction) can be utilized in the manner described above, to identify the presence of a deletion, addition, or substitution of one or more nucleotides within any one of the exons of endoglin, RI, RII, or betaglycan. Following the PCR reaction, the PCR product can be analyzed by methods as described above, such as the heteroduplex detection technique based upon that of White et al. (Genomics 12:301–306, 1992), or by techniques such as cleavage of RNA-DNA hybrids using RNase A (Myers et al., Science 230:1242–1246, 1985); single-stranded conformation polymorphism (SSCP) analysis (Orita et al., Genomics 10:298–299, 1989); and denaturing gradient gel electrophoresis (DGGE; Myers et al., Methods Enzymol. 155:501–527, 1987). The PCR may be carried out using a primer which adds a G+C-rich sequence (termed a "GC-clamp") to one end of the PCR product, thus improving the sensitivity of the subsequent DGGE procedure (Sheffield et al., Proc. Natl. Acad. Sci. USA 86:232–236, 1989). If the particular mutation present in the patient's family is known to have removed or added a restriction site, or to have significantly increased or decreased the length of a particular restriction fragment, a protocol based upon restriction fragment length polymorphism (RFLP) analysis (perhaps combined with PCR) may be appropriate. The apparent genetic heterogeneity of the HHT phenotype means that the nature of the particular mutation carried by affected individuals in the patient's family may have to be ascertained (e.g., by methods as described above) prior to attempting genetic diagnosis of the patient. Alternatively, a battery of tests designed to identify any of several mutations known to result in HHT may be utilized to screen individuals without a defined familial genotype. The analysis can be carried out on any genomic DNA derived from the patient, typically from a blood sample.

As discussed above, the genetic defect underlying the HHT phenotype may be in an endoglin gene, or in any of the other components of the TGF-β receptor complex. A given family may harbor a defective gene encoding the type I receptor (Frazen et al., Cell 75:681–692, 1993), type II receptor (Lin et al., Cell 68:775–785, 1992), betaglycan (Wang et al., Cell 67:797–805, 1991; Lopez-Casillas et al., Cell 67:785–795, 1991; Moren et al., Biochem. Biophys. Res. Commun. 189:356–362, 1992), or the type I TGF-β/activin receptor (TSR-I; Attisano et al., Cell 75:671–680, 1993). Mutations in each of these genes may be assayed by methods similar to those described herein. If a given family's particular defect has not yet been characterized, selection of the gene most likely to be the source of the defect may be guided by genetic linkage analysis, using appropriate markers.

Instead of basing the diagnosis of HHT on analysis of the genomic DNA of a patient, one could seek evidence of the mutation in the level or nature of the relevant expression products. Unlike genomic DNA-based diagnostic methods, this approach permits detection of defects resulting in a decrease in the level of expression of the affected gene (e.g., endoglin) which do not involve mutations in the coding sequence itself. An analysis of expression requires use of cells that normally express the gene of interest in detectable amounts. For endoglin, that has meant vascular endothelial cells of capillaries, arterioles and venules, or possibly fibroblasts. A useful source of such cells would be the umbilical cord and/or placenta of a newborn, which could be harvested at birth and stored frozen until needed for the diagnostic tests. Recently, endoglin was also found to be expressed in cells within the "buffy coat" of peripheral blood, i.e., white blood cells isolated by density centrifugation of whole blood. This readily available source of endoglin mRNA has obvious advantages over tissues that must be harvested perinatally and stored.

Well-known techniques for analyzing expression include mRNA-based methods, such as Northern blots and in situ hybridization (using a nucleic acid probe derived from the relevant cDNA), and quantitative PCR (as described in St-Jacques et al., Endocrinology 134:2645–2657, 1994). One also could employ polypeptide-based methods, including use of antibodies specific for the polypeptide of interest. These techniques permit quantitation of the amount of expression of a given gene in the tissue of interest, at least relative to positive and negative controls. One would expect an individual who is heterozygous for a genetic defect affecting level of expression of endoglin to show up to a 50% loss of expression of this gene in such a hybridization or antibody-based assay. An antibody specific for the carboxy terminal end would be likely to pick up (by failure to bind to) most or all frame-shift and premature termination signal mutations, as well as deletions of the carboxy terminal sequence. Use of a battery of monoclonal antibodies specific for different epitopes of endoglin would be useful for rapidly screening cells to detect those expressing mutant forms of endoglin (i.e., cells which bind to some endoglin-specific MAbs, but not to others), or for quantifying the level of endoglin on the surface of the cells.

Another type of polypeptide-based assay would measure loss of function. For example, one might determine whether the patient's endoglin-expressing cells bind and/or respond to TGF-β in a manner similar to cells from a normal individual. Binding of TGF-β could be measured using a radiolabelled ligand or ELISA (for example, see Cheifetz et al., J. Biol. Chem. 269:1995–2001, 1994), while response to the ligand could be measured by a standard TGF-β biological assay, e.g. as discussed in Madri et al., Annals of the New York Academy of Science 593:243–258, 1990 (herein incorporated by reference). A significant degree of loss of function (e.g., at least 50%) indicates that the patient bears at least one genetic defect in a gene involved in the TGF-β response, and is indicative of HHT. Since endoglin forms homodimers, it may be that one defective endoglin gene acts as a dominant negative mutant, suppressing the activity of the normal allele. If so, the level of functional dimeric endoglin would be something less than 50% of the normal level (e.g., 10–30%), even though only one allele is defective.

Finally, one could use a protein truncation assay (Heim et al., Nature Genetics 8:218–219, 1994) to screen for any genetic defect which results in the production of a truncated polypeptide instead of the wildtype protein.

EXAMPLE 2

Genetic Therapy

A patient with HHT can be treated by supplying a functional gene encoding the defective component of the TGF-β receptor complex. Following diagnosis to determine which gene of the complex is defective in a given patient, a DNA (e.g., a cDNA) is prepared which encodes the wildtype form of the gene operably linked to expression control elements (e.g., promoter and enhancer) that induce expression in endothelial cells, peripheral blood cells or any other affected cells. Examples of expression control elements that would be useful in targeting endothelial cells include those associated with the genes encoding endoglin; tie-2 (Schnurch and Risau, Development 119:957–968, 1993); the vascular endothelial growth factor (VEGF) receptor Flk-1 (Millauer et al., Cell 72:835–846, 1993); and the Tek endothelial cell receptor (Dumont et al., Genes & Development 8:1897–1909, 1994). The DNA may be incorporated into a vector appropriate for transforming the cells, such as a retrovirus, adenovirus or adeno-associated virus. Alternatively, one of the many other known types of techniques for introducing DNA into cells in vivo may be used: e.g., liposomes. The presence of the target endothelial cells in the lining of the patient's blood vessels means that the DNA may be administered to the patient by the simple means of intravenous injection, whereupon it should travel throughout the bloodstream and contact essentially all of the intended target cells. In such a protocol, it is expected that approximately 1 to 100 μg/kg body weight would be an effective amount of cDNA.

One could instead rely on local injections into the surface lesions and catheter-delivered infusions directly into the deeper lesions (e.g., PAVMs), repeating the treatment as necessary to achieve the desired response. The catheter could be coupled with a pair of balloons to trap the infusion in a particular region of the blood vessel until the DNA can enter the endothelial cells at the site of the telangiecstasis. Approximately 1 to 10 molecules of DNA per endothelial cell, or about $10^3$ to $10^6$ per telangiectasis, would be an adequate dose.

EXAMPLE 3

TGF-β Treatment

Because the defect in HHT is attributable to the inability of vascular endothelial cells to respond to TGF-β, it is expected that the function of these cells can be improved by increasing the amount of TGF-β present at the cellular surface. Thus, patients suffering from the symptoms of HHT can be treated with TGF-β, preferably by local injection at the site of the telangiecstasis, or by applying a TGF-β-containing ointment or dressing to the skin or mucous membrane at the site of the lesion. This may be particularly appropriate for treating the frequent nosebleeds which often accompany HHT. Where the genetic defect is in an endoglin gene, TGF-β1 or TGF-β3 may be used.

EXAMPLE 4

Animal Model

A line of transgenic animals (e.g., mice, rats, guinea pigs, hamsters, rabbits, or other mammals) could be produced bearing a transgene encoding a defective form of endoglin which retains the ability to dimerize with the wildtype monomer, but which is biologically inactive and forms inactive dimers. Such a mutant form of endoglin would act as a dominant-negative mutant, suppressing the activity of the wildtype alleles and permitting use of the animal as a model system for studying HHT and potential therapy therefor. Standard methods of generating such transgenic animals would be used, e.g. as described in Leder et al., U.S. Pat. No. 4,736,866.

Alternatively, standard methods of producing null mice could be used to generate a mouse which bears one defective and one wildtype allele encoding endoglin. It is expected that such a mouse would be susceptible to developing the symptoms which characterize HHT in humans heterozygous for a mutant endoglin gene, and so would serve as a useful animal model for the disease. If desired, two such heterozygous mice could be crossed to produce offspring which are homozygous for the mutant allele.

Other embodiments are within the following claims.

Under the terms of the Budapest Treaty on the International Recognition of the Deposit of Microorganisms for the Purpose of Patent Procedure, deposit of cosmid 21c10 has been made with the American Type Culture Collection (ATCC) of Manassas, Va., where the deposit was given Accession Number 98685.

Applicants' assignees, Duke University and HSC Research & Development Limited Partnership, represent that the ATCC is a depository affording permanence of the deposit and ready accessibility thereto by the public if a patent is granted. All restrictions on the availability to the public of the material so deposited have been irrevocably removed. The material will be available during the pendency of the patent application to one determined by the Commissioner to be entitled thereto under 37 C.F.R. §1.14 and 35 U.S.C. §1.22. The deposited material will be maintained with all the care necessary to keep it viable and uncontaminated for a period of at least five years after the most recent request for the furnishing of a sample of the deposited material, and in any case, for a period of at least thirty (30) years after the date of deposit or for the enforceable life of the patent, whichever period is longer. Applicants acknowledge their duty to replace the deposit should the depository be unable to furnish a sample when requested due to the condition of the deposit.

What is claimed is:

1. A diagnostic method comprising determining whether a sample of genomic DNA provided from a patient or fetus suspected of being susceptible to hereditary haemorrhagic telangiectasia (HHT) comprises a mutation in a gene encoding endoglin, said mutation being an indication that said patient or fetus is susceptible to HHT.

2. The method of claim 1, wherein said method includes the step of treating said sample of genomic DNA with a restriction enzyme selected from the group consisting of MaeIII and BbvI.

3. The method of claim 1, wherein said method includes the step of subjecting said sample to polymerase chain reaction (PCR), using a forward PCR primer complementary to a portion of the antisense strand of said gene, said portion being within (a) a first intron of said gene, or (b) the 5' untranslated region adjacent to the start codon of said gene; and a reverse PCR primer complementary to a fragment of the sense strand of said gene, said fragment being within (a) a second intron of said gene, or (b) the 3' untranslated region adjacent to the termination codon of said gene.

4. The method of claim 1, wherein said sample is obtained by amniocentesis or chorionic villi sampling.

5. A diagnostic method comprising determining whether endoglin mRNA provided from a patient or fetus comprises a mutation, the presence of the mutation indicating that the patient or fetus is genetically predisposed to developing the HHT phenotype.

6. The method of claim 5, wherein said mRNA is obtained from a tissue comprising peripheral blood.

7. The method of claim 5, wherein said mutation is detected by examining the sequence of cDNA obtained by subjecting endoglin mRNA to reverse transcription-PCR (RT-PCR).

8. The method of claim 5, further comprising identifying a patient or fetus suspected of being genetically predisposed to developing the HHT phenotype; and obtaining from said patient or fetus a sample of mRNA from a tissue which normally expresses a gene of the TGF-β receptor complex.

9. A diagnostic method comprising determining whether a sample of genomic DNA obtained from a patient or fetus comprises a mutation in a gene encoding betaglycan, TGF-β type II receptor (RII), or TGF-β/activin type I receptor (TSR-I), said mutation being an indication that the patient or fetus is susceptible to hereditary haemorrhagic telangiectasia.

10. The method of claim 9, comprising determining whether genomic DNA obtained from the patent or fetus includes a mutation in a gene encoding TSR-I.

11. A diagnostic method comprising determining whether betaglycan mRNA, TGF-β type II receptor (RII) mRNA, or TGF-β/activin type I receptor (TSR-I) mRNA obtained from a patient or fetus includes a mutation, the presence of the mutation indicating that the patient or fetus is genetically predisposed to developing the HHT phenotype.

12. The method of claim 11, comprising determining whether mRNA obtained from the patent or fetus includes a mutation in a gene encoding TSR-I.

* * * * *

Disclaimer

6,022,687— Michelle Letarte, Toronto, Canada; Douglas A. Marchuk, Chapel Hill; Kimberly McAllister, Durham, both of N.C. DIAGNOSIS OF AND THERAPY FOR HEREDITARY HAEMORRHAGIC TELANGIECTASIA. Patent dated Feb. 8, 2000. Disclaimer filed Jul. 21, 2003, by the Assignee, Duke University.

Hereby enters this disclaimer to claims 1-12, of said patent.

*(Official Gazette, October 7, 2003)*

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
      (A) LENGTH: 2025 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: Coding Sequence
      (B) LOCATION: 1...1974

(xi) SEQUENCE DESCRIPTION: SEQ ID NO:1:

```
ATG GAC CGC GGC ACG CTC CCT CTG GCT GTT GCC CTG CTG CTG GCC AGC        48
Met Asp Arg Gly Thr Leu Pro Leu Ala Val Ala Leu Leu Leu Ala Ser
 1               5                  10                  15

TGC AGC CTC AGC CCC ACA AGT CTT GCA GAA ACA GTC CAT TGT GAC CTT        96
Cys Ser Leu Ser Pro Thr Ser Leu Ala Glu Thr Val His Cys Asp Leu
            20                  25                  30

CAG CCT GTG GGC CCC GAG AGG GGC GAG GTG ACA TAT ACC ACT AGC CAG       144
Gln Pro Val Gly Pro Glu Arg Gly Glu Val Thr Tyr Thr Thr Ser Gln
        35                  40                  45

GTC TCG AAG GGC TGC GTG GCT CAG GCC CCC AAT GCC ATC CTT GAA GTC       192
Val Ser Lys Gly Cys Val Ala Gln Ala Pro Asn Ala Ile Leu Glu Val
    50                  55                  60

CAT GTC CTC TTC CTG GAG TTC CCA ACG GGC CCG TCA CAG CTG GAG CTG       240
His Val Leu Phe Leu Glu Phe Pro Thr Gly Pro Ser Gln Leu Glu Leu
65                  70                  75                  80

ACT CTC CAG GCA TCC AAG CAA AAT GGC ACC TGG CCC CGA GAG GTG CTT       288
Thr Leu Gln Ala Ser Lys Gln Asn Gly Thr Trp Pro Arg Glu Val Leu
                85                  90                  95

CTG GTC CTC AGT GTA AAC AGC AGT GTC TTC CTG CAT CTC CAG GCC CTG       336
Leu Val Leu Ser Val Asn Ser Ser Val Phe Leu His Leu Gln Ala Leu
            100                 105                 110
```

-continued

| | | |
|---|---|---|
| GGA ATC CCA CTG CAC TTG GCC TAC AAT TCC AGC CTG GTC ACC TTC CAA<br>Gly Ile Pro Leu His Leu Ala Tyr Asn Ser Ser Leu Val Thr Phe Gln<br>115                    120                    125 | 384 |
| GAG CCC CCG GGG GTC AAC ACC ACA GAG CTG CCA TCC TTC CCC AAG ACC<br>Glu Pro Pro Gly Val Asn Thr Thr Glu Leu Pro Ser Phe Pro Lys Thr<br>130                    135                    140 | 432 |
| CAG ATC CTT GAG TGG GCA GCT GAG AGG GGC CCC ATC ACC TCT GCT GCT<br>Gln Ile Leu Glu Trp Ala Ala Glu Arg Gly Pro Ile Thr Ser Ala Ala<br>145                    150                    155                    160 | 480 |
| GAG CTG AAT GAC CCC CAG AGC ATC CTC CTC CGA CTG GGC CAA GCC CAG<br>Glu Leu Asn Asp Pro Gln Ser Ile Leu Leu Arg Leu Gly Gln Ala Gln<br>                    165                    170                    175 | 528 |
| GGG TCA CTG TCC TTC TGC ATG CTG GAA GCC AGC CAG GAC ATG GGC CGC<br>Gly Ser Leu Ser Phe Cys Met Leu Glu Ala Ser Gln Asp Met Gly Arg<br>                    180                    185                    190 | 576 |
| ACG CTC GAG TGG CGG CCG CGT ACT CCA GCC TTG GTC CGG GGC TGC CAC<br>Thr Leu Glu Trp Arg Pro Arg Thr Pro Ala Leu Val Arg Gly Cys His<br>                    195                    200                    205 | 624 |
| TTG GAA GGC GTG GCC GGC CAC AAG GAG GCG CAC ATC CTG AGG GTC CTG<br>Leu Glu Gly Val Ala Gly His Lys Glu Ala His Ile Leu Arg Val Leu<br>                    210                    215                    220 | 672 |
| CCG GGC CAC TCG GCC GGG CCC CGG ACG GTG ACG GTG AAG GTG GAA CTG<br>Pro Gly His Ser Ala Gly Pro Arg Thr Val Thr Val Lys Val Glu Leu<br>225                    230                    235                    240 | 720 |
| AGC TGC GCA CCC GGG GAT CTC GAT GCC GTC CTC ATC CTG CAG GGT CCC<br>Ser Cys Ala Pro Gly Asp Leu Asp Ala Val Leu Ile Leu Gln Gly Pro<br>                                245                    250                    255 | 768 |
| CCC TAC GTG TCC TGG CTC ATC GAC GCC AAC CAC AAC ATG CAG ATC TGG<br>Pro Tyr Val Ser Trp Leu Ile Asp Ala Asn His Asn Met Gln Ile Trp<br>                    260                    265                    270 | 816 |
| ACC ACT GGA GAA TAC TCC TTC AAG ATC TTT CCA GAG AAA AAC ATT CGT<br>Thr Thr Gly Glu Tyr Ser Phe Lys Ile Phe Pro Glu Lys Asn Ile Arg<br>                    275                    280                    285 | 864 |
| GGC TTC AAG CTC CCA GAC ACA CCT CAA GGC CTC CTG GGG GAG GCC CGG<br>Gly Phe Lys Leu Pro Asp Thr Pro Gln Gly Leu Leu Gly Glu Ala Arg<br>                    290                    295                    300 | 912 |
| ATG CTC AAT GCC AGC ATT GTG GCA TCC TTC GTG GAG CTA CCG CTG GCC<br>Met Leu Asn Ala Ser Ile Val Ala Ser Phe Val Glu Leu Pro Leu Ala<br>305                    310                    315                    320 | 960 |
| AGC ATT GTC TCA CTT CAT GCC TCC AGC TGC GGT GGT AGG CTG CAG ACC<br>Ser Ile Val Ser Leu His Ala Ser Ser Cys Gly Gly Arg Leu Gln Thr<br>                              325                    330                    335 | 1008 |
| TCA CCC GCA CCG ATC CAG ACC ACT CCT CCC AAG GAC ACT TGT AGC CCG<br>Ser Pro Ala Pro Ile Gln Thr Thr Pro Pro Lys Asp Thr Cys Ser Pro<br>                                340                    345                    350 | 1056 |
| GAG CTG CTC ATG TCC TTG ATC CAG ACA AAG TGT GCC GAC GAC GCC ATG<br>Glu Leu Leu Met Ser Leu Ile Gln Thr Lys Cys Ala Asp Asp Ala Met<br>                    355                    360                    365 | 1104 |
| ACC CTG GTA CTA AAG AAA GAG CTT GTT GCG CAT TTG AAG TGC ACC ATC<br>Thr Leu Val Leu Lys Lys Glu Leu Val Ala His Leu Lys Cys Thr Ile<br>                          370                    375                    380 | 1152 |
| ACG GGC CTG ACC TTC TGG GAC CCC AGC TGT GAG GCA GAG GAC AGG GGT<br>Thr Gly Leu Thr Phe Trp Asp Pro Ser Cys Glu Ala Glu Asp Arg Gly<br>385                    390                    395                    400 | 1200 |
| GAC AAG TTT GTC TTG CGC AGT GCT TAC TCC AGC TGT GGC ATG CAG GTG<br>Asp Lys Phe Val Leu Arg Ser Ala Tyr Ser Ser Cys Gly Met Gln Val<br>                                405                    410                    415 | 1248 |
| TCA GCA AGT ATG ATC AGC AAT GAG GCG GTG GTC AAT ATC CTG TCG AGC<br>Ser Ala Ser Met Ile Ser Asn Glu Ala Val Val Asn Ile Leu Ser Ser<br>                    420                    425                    430 | 1296 |

```
TCA TCA CCA CAG CGG AAA AAG GTG CAC TGC CTC AAC ATG GAC AGC CTC      1344
Ser Ser Pro Gln Arg Lys Lys Val His Cys Leu Asn Met Asp Ser Leu
        435                 440                 445

TCT TTC CAG CTG GGC CTC TAC CTC AGC CCA CAC TTC CTC CAG GCC TCC      1392
Ser Phe Gln Leu Gly Leu Tyr Leu Ser Pro His Phe Leu Gln Ala Ser
450                 455                 460

AAC ACC ATC GAG CCG GGG CAG CAG AGC TTT GTG CAG GTC AGA GTG TCC      1440
Asn Thr Ile Glu Pro Gly Gln Gln Ser Phe Val Gln Val Arg Val Ser
465                 470                 475                 480

CCA TCC GTC TCC GAG TTC CTG CTC CAG TTA GAC AGC TGC CAC CTG GAC      1488
Pro Ser Val Ser Glu Phe Leu Leu Gln Leu Asp Ser Cys His Leu Asp
                485                 490                 495

TTG GGG CCT GAG GGA GGC ACC GTG GAA CTC ATC CAG GGC CGG GCG GCC      1536
Leu Gly Pro Glu Gly Gly Thr Val Glu Leu Ile Gln Gly Arg Ala Ala
            500                 505                 510

AAG GGC AAC TGT GTG AGC CTG CTG TCC CCA AGC CCC GAG GGT GAC CCG      1584
Lys Gly Asn Cys Val Ser Leu Leu Ser Pro Ser Pro Glu Gly Asp Pro
                515                 520                 525

CGC TTC AGC TTC CTC CTC CAC TTC TAC ACA GTA CCC ATA CCC AAA ACC      1632
Arg Phe Ser Phe Leu Leu His Phe Tyr Thr Val Pro Ile Pro Lys Thr
530                 535                 540

GGC ACC CTC AGC TGC ACG GTA GCC CTG CGT CCC AAG ACC GGG TCT CAA      1680
Gly Thr Leu Ser Cys Thr Val Ala Leu Arg Pro Lys Thr Gly Ser Gln
545                 550                 555                 560

GAC CAG GAA GTC CAT AGG ACT GTC TTC ATG CGC TTG AAC ATC ATC AGC      1728
Asp Gln Glu Val His Arg Thr Val Phe Met Arg Leu Asn Ile Ile Ser
                565                 570                 575

CCT GAC CTG TCT GGT TGC ACA AGC AAA GGC CTC GTC CTG CCC GCC GTG      1776
Pro Asp Leu Ser Gly Cys Thr Ser Lys Gly Leu Val Leu Pro Ala Val
            580                 585                 590

CTG GGC ATC ACC TTT GGT GCC TTC CTC ATC GGG GCC CTG CTC ACT GCT      1824
Leu Gly Ile Thr Phe Gly Ala Phe Leu Ile Gly Ala Leu Leu Thr Ala
                595                 600                 605

GCA CTC TGG TAC ATC TAC TCG CAC ACG CGT TCC CCC AGC AAG CGG GAG      1872
Ala Leu Trp Tyr Ile Tyr Ser His Thr Arg Ser Pro Ser Lys Arg Glu
610                 615                 620

CCC GTG GTG GCG GTG GCT GCC CCG GCC TCC TCG GAG AGC AGC AGC ACC      1920
Pro Val Val Ala Val Ala Ala Pro Ala Ser Ser Glu Ser Ser Ser Thr
625                 630                 635                 640

AAC CAC AGC ATC GGG AGC ACC CAG AGC ACC CCC TGC TCC ACC AGC AGC      1968
Asn His Ser Ile Gly Ser Thr Gln Ser Thr Pro Cys Ser Thr Ser Ser
                645                 650                 655

ATG GCA TAGCCCCGGC CCCCCGCGCT CGCCCAGCAG GAGAGACTGA GCAGCCGCCA G      2025
Met Ala (2) INFORMATION FOR SEQ ID NO:2:

(i) SEQUENCE CHARACTERISTICS:
        (A) LENGTH: 658 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:2:

Met Asp Arg Gly Thr Leu Pro Leu Ala Val Ala Leu Leu Leu Ala Ser
 1               5                  10                  15

Cys Ser Leu Ser Pro Thr Ser Leu Ala Glu Thr Val His Cys Asp Leu
                20                  25                  30

Gln Pro Val Gly Pro Glu Arg Gly Glu Val Thr Tyr Thr Thr Ser Gln
```

```
                    35                  40                  45
Val Ser Lys Gly Cys Val Ala Gln Ala Pro Asn Ala Ile Leu Glu Val
     50                  55                  60
His Val Leu Phe Leu Glu Phe Pro Thr Gly Pro Ser Gln Leu Glu Leu
 65                  70                  75                  80
Thr Leu Gln Ala Ser Lys Gln Asn Gly Thr Trp Pro Arg Glu Val Leu
                 85                  90                  95
Leu Val Leu Ser Val Asn Ser Ser Val Phe Leu His Leu Gln Ala Leu
                100                 105                 110
Gly Ile Pro Leu His Leu Ala Tyr Asn Ser Ser Leu Val Thr Phe Gln
            115                 120                 125
Glu Pro Pro Gly Val Asn Thr Thr Glu Leu Pro Ser Phe Pro Lys Thr
130                 135                 140
Gln Ile Leu Glu Trp Ala Ala Glu Arg Gly Pro Ile Thr Ser Ala Ala
145                 150                 155                 160
Glu Leu Asn Asp Pro Gln Ser Ile Leu Leu Arg Leu Gly Gln Ala Gln
                165                 170                 175
Gly Ser Leu Ser Phe Cys Met Leu Glu Ala Ser Gln Asp Met Gly Arg
            180                 185                 190
Thr Leu Glu Trp Arg Pro Arg Thr Pro Ala Leu Val Arg Gly Cys His
            195                 200                 205
Leu Glu Gly Val Ala Gly His Lys Glu Ala His Ile Leu Arg Val Leu
210                 215                 220
Pro Gly His Ser Ala Gly Pro Arg Thr Val Thr Val Lys Val Glu Leu
225                 230                 235                 240
Ser Cys Ala Pro Gly Asp Leu Asp Ala Val Leu Ile Leu Gln Gly Pro
                245                 250                 255
Pro Tyr Val Ser Trp Leu Ile Asp Ala Asn His Asn Met Gln Ile Trp
            260                 265                 270
Thr Thr Gly Glu Tyr Ser Phe Lys Ile Phe Pro Glu Lys Asn Ile Arg
            275                 280                 285
Gly Phe Lys Leu Pro Asp Thr Pro Gln Gly Leu Leu Gly Glu Ala Arg
            290                 295                 300
Met Leu Asn Ala Ser Ile Val Ala Ser Phe Val Glu Leu Pro Leu Ala
305                 310                 315                 320
Ser Ile Val Ser Leu His Ala Ser Ser Cys Gly Gly Arg Leu Gln Thr
                325                 330                 335
Ser Pro Ala Pro Ile Gln Thr Thr Pro Pro Lys Asp Thr Cys Ser Pro
            340                 345                 350
Glu Leu Leu Met Ser Leu Ile Gln Thr Lys Cys Ala Asp Asp Ala Met
            355                 360                 365
Thr Leu Val Leu Lys Lys Glu Leu Val Ala His Leu Lys Cys Thr Ile
            370                 375                 380
Thr Gly Leu Thr Phe Trp Asp Pro Ser Cys Glu Ala Glu Asp Arg Gly
385                 390                 395                 400
Asp Lys Phe Val Leu Arg Ser Ala Tyr Ser Ser Cys Gly Met Gln Val
                405                 410                 415
Ser Ala Ser Met Ile Ser Asn Glu Ala Val Val Asn Ile Leu Ser Ser
            420                 425                 430
Ser Ser Pro Gln Arg Lys Lys Val His Cys Leu Asn Met Asp Ser Leu
            435                 440                 445
Ser Phe Gln Leu Gly Leu Tyr Leu Ser Pro His Phe Leu Gln Ala Ser
            450                 455                 460
```

```
Asn Thr Ile Glu Pro Gly Gln Gln Ser Phe Val Gln Val Arg Val Ser
465                 470                 475                 480

Pro Ser Val Ser Glu Phe Leu Leu Gln Leu Asp Ser Cys His Leu Asp
            485                 490                 495

Leu Gly Pro Glu Gly Gly Thr Val Glu Leu Ile Gln Gly Arg Ala Ala
            500                 505                 510

Lys Gly Asn Cys Val Ser Leu Leu Ser Pro Ser Pro Glu Gly Asp Pro
            515                 520                 525

Arg Phe Ser Phe Leu Leu His Phe Tyr Thr Val Pro Ile Pro Lys Thr
            530                 535                 540

Gly Thr Leu Ser Cys Thr Val Ala Leu Arg Pro Lys Thr Gly Ser Gln
545                 550                 555                 560

Asp Gln Glu Val His Arg Thr Val Phe Met Arg Leu Asn Ile Ile Ser
            565                 570                 575

Pro Asp Leu Ser Gly Cys Thr Ser Lys Gly Leu Val Leu Pro Ala Val
            580                 585                 590

Leu Gly Ile Thr Phe Gly Ala Phe Leu Ile Gly Ala Leu Leu Thr Ala
            595                 600                 605

Ala Leu Trp Tyr Ile Tyr Ser His Thr Arg Ser Pro Ser Lys Arg Glu
            610                 615                 620

Pro Val Val Ala Val Ala Ala Pro Ala Ser Ser Glu Ser Ser Ser Thr
625                 630                 635                 640

Asn His Ser Ile Gly Ser Thr Gln Ser Thr Pro Cys Ser Thr Ser Ser
            645                 650                 655

Met Ala (2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:3:

ACTGGAGAAT ACTCCTTCAA G                                                21

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:4:

ACTGGAGAAT AGTCCTTCAA G                                                21

(2) INFORMATION FOR SEQ ID NO:5:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:5:
```

CTCCCAGACA CACCTCAAGG CCTCCTGGGG GAGGCCCGGA TGCTCAATGC CAGCATT                57

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:6:

CTCCCAGATG CCAGCATT                                                           18

(2) INFORMATION FOR SEQ ID NO:7:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:7:

AACTGTGTGA GCCTGCTGTC CCCAAGCCCC GAGGGTGAC                                    39

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:8:

AACTGTGTGA CTGCTGTCCC CAAGCCCCGA GGGTGA                                       36

(2) INFORMATION FOR SEQ ID NO:9:

(i) SEQUENCE CHARACTERISTICS:
        (A) LENGTH: 67 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:9:

ATGGACCGCG GCACGCTCCC TCTGGCTGTT GCCCTGCTGC TGGCCAGCTG CAGCCTCAGC             60

CCCACAA                                                                       67

(2) INFORMATION FOR SEQ ID NO:10:

(i) SEQUENCE CHARACTERISTICS:
        (A) LENGTH: 484 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:10:

AATCCATGGA ACGAATATAA TGATATCACC TCATAAGGTG GCTGTGATGA TGCAGGAAAG             60

| | |
|---|---:|
| CNGTTAGCTC ATGTCAAGTC CCTAGGAGAC GTTTGGAAAG TAGGAGTCAT TGTCATCACC | 120 |
| TTATTCTCAC CTGGCCTCTT TCCGGATGTT TCTCCAACAG GTCTTGCAGA AACAGTCCAT | 180 |
| TGTGACCTTC AGCCTGTGGG CCCCGAGAGG GGCGAGGTGA CATATACCAC TAGCCAGGTC | 240 |
| TCGAAGGGCT GCGTGGCTCA GGCCCCCAAT GCCATCCTTG AAGTCCATGT CCTCTTCCTG | 300 |
| GAGTTCCCAA CGGTGAGTGT CCCATGGCAG GGTCGGGTGG GGGCTCAGAG GAAGCTCCAA | 360 |
| GGCAGATGGG GTGAGGGGTG CCTTCCTTGT GGCTGTCCCT GGGGCAGTGG CTGAGTCCTC | 420 |
| GTTAGCCCCC TGCCAAGAGA GTGATGTGGG CATCTCACAG GGCCCATAAG AGGTGGCATT | 480 |
| TCTA | 484 |

(2) INFORMATION FOR SEQ ID NO:11:

(i) SEQUENCE CHARACTERISTICS:
        (A) LENGTH: 141 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:11:

| | |
|---|---:|
| GGCCCGTCAC AGCTGGAGCT GACTCTCCAG GCATCCAAGC AAAATGGCAC CTGGCCCCGA | 60 |
| GAGGTGCTTC TGGTCCTCAG TGTAAACAGC AGTGTCTTCC TGCATCTCCA GGCCCTGGGA | 120 |
| ATCCCACTGC ACTTGGCCTA C | 141 |

(2) INFORMATION FOR SEQ ID NO:12:

(i) SEQUENCE CHARACTERISTICS:
        (A) LENGTH: 496 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:12:

| | |
|---|---:|
| GGCCTCTTTC TCTCAGCCAA TGGGCTGACT CCACAAATTA CTTCCTGACC TCCTACATGG | 60 |
| GATAGAGAGG GCACAGGGCA GGAACAGCGT GCTGAGCCTC CACATGTCTC CCCAGAATTC | 120 |
| CAGCCTGGTC ACCTTCCAAG AGCCCCCGGG GGTCAACACC ACAGAGCTGC CATCCTTCCC | 180 |
| CAAGACCCAG ATCCTTGAGT GGGCAGCTGA GAGGGGCCCC ATCACCTCTG CTGCTGAGCT | 240 |
| GAATGACCCC CAGAGCATCC TCCTCCGACT GGGCCAAGGT CAGTTTCCCC AGCAACCTCT | 300 |
| CTGGGCCTCA TGATACTGCT CAGGAGGAAT CTGAGCTCCT CTGGCCCACA CCTCAAACTT | 360 |
| GGGCACCAAG AGTGCAGGAG GGGACACGCT GTGCCACAGT TCACATGCCA CAAGCCAGTG | 420 |
| CTGCCTTGGG ACAGTGATGG CTCCTCCACC AAATATCAGA TTGAAGCATG TGGAATATGC | 480 |
| CAGGTTCTGA CCTAAA | 496 |

(2) INFORMATION FOR SEQ ID NO:13:

(i) SEQUENCE CHARACTERISTICS:
        (A) LENGTH: 135 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:13:

| | |
|---|---:|
| TTGGCAGGTA GTGGTGGAAG GGAAGTTCGA ACCTAGGTCC TCTGAGCCTC TCCCCTCTGC | 60 |

AGCACCGTCC TGCCTGCCCC ACCACTATCT TTGGCTGTGG GTGAGGGCGG GCTCTGTTAG    120

GTGCAGGGCT GCTGA    135

(2) INFORMATION FOR SEQ ID NO:14:

(i) SEQUENCE CHARACTERISTICS:
        (A) LENGTH: 1817 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:14:

CCCAGGGGTC ACTGTCCTTC TGCATGCTGG AAGCCAGCCA GGACATGGGC CGCACGCTCG    60

AGTGGCGGCC GCGTACTCCA GCCTTGGTCC GGGGCTGCCA CTTGGAAGGC GTGGCCGGCC    120

ACAAGGAGGC GCACATCCTG AGGGTCCTGC CGGGCCACTC GGCCGGGTAT GGCTCTCGCC    180

CCGCCCCTGA CACTAGTCCC CACCCCGAGA GACCACCCCC CTGACCCCCC CCCGCCCCCT    240

CTCCGGTCCC TTATAAAGCC CCACCCCAGT CCCAGACCCA GCCCCGCCGC AGCCCTGTGA    300

GAGCACAGTC GCTTTCTCCT ACTCTAGGCT ACGCCCCCTA TGGGCCCCTT CCCTTTGGGC    360

ACAAGCCTGG CCCCAGTCCC ATCCCTATCC CATAAACCCA CACCTGGCCA GGTAAGAGTG    420

CAGCCGCCGC CCACCCGACG CCAGGCCTCG CTCCCCGCCT GGCCTGTCCG CTTCAGTGTT    480

CCATCCGCGT CTGTCTCCCC GCAGGCCCCG GACGGTGACG GTGAAGGTGG AACTGAGCTG    540

CGCACCCGGG GATCTCGATG CCGTCCTCAT CCTGCAGGGT CCCCCCTACG TGTCCTGGCT    600

CATCGACGCC AACCACAACA TGCAGATCTG GGTGAGTTGT GCGCAGCTCC CGGGACACAA    660

AACCCAAACT CCCAACCTCT GGATCAGGGA AGTTTCCTGG AAAGGTGAAC CCCCGAGTTG    720

AGCTGAAGGA CAAATCACCT ATGCCCATAC GTGAGGGAAG GGGCCAGGCA GAAGACGCAG    780

CAGGAGTGGG GACACAGCAG GACCGAGGCC TGGCATAACC CTGGCTGGCC TGCTGTGGCA    840

CAGACTGTGT CCATGGCCCC CTGTTCTGCC TCTCTCCCCA CCATTAGACC ACTGGAGAAT    900

ACTCCTTCAA GATCTTTCCA GAGAAAAACA TTCGTGGCTT CAAGCTCCCA GACACACCTC    960

AAGGCCTCCT GGGGGAGGCC CGGATGCTCA ATGCCAGCAT TGTGGCATCC TTCGTGGAGC    1020

TACCGCTGGC CAGCATTGTC TCACTTCATG CCTCCAGCTG CGGTGAGCAC CCTTCCCCTG    1080

CCCCTCCCTT CCCTTCCCCT CCCTTGGATC AGTGGCCACA CTGTTGGTGA AGCACCTCTG    1140

TGTGAGCTTG GGCAAGGTAC ATCAGCCTCT CTGAGCCTCA TTTTTCTCAT CTGCACATGG    1200

GAACAATGGG AGTAGCTAAT CATAGAAGAG CCTGAGAATC GCTTGAACCT GGGAGATGGA    1260

GGTTGCAGTG AGCCAAGATC GTGCCACTGC ACTCCCAGCC CGGGTAACAG AGCAAAACTC    1320

CGTCTCAAAA AAAAAAAAA AAAAAAAAAA GCCTGGTGCG GCACACATAT CACACAGTGA    1380

CCAGCCGCCT GGCCTGCCTC TNCNACCCCA CAGGTGGTAG GCTGCAGACC TCACCCGCAC    1440

CGATCCAGAC CACTCCTCCC AAGGACACTT GTAGCCCGGA GCTGCTCATG TCCTTGATCC    1500

AGACAAAGTG TGCCGACGAC GCCATGACCC TGGTACTAAA GAAAGAGCTT GTTGCGGTAA    1560

GGGAACTCCT GCCCCTCTGG CTCAGGATGA CATGGACATC TGGTTCCTCC CCTAGCCAAG    1620

ACTCTTGGGG TCCTAGCCCA GGCAGGGGGG CAAGTCACGT CCCTCTGCAA GCCTTAGTTT    1680

TCCCACTTGT ATAATGGAAT TGATAATGGT ACCTACCACG TGGTGAGAAT TAAAGGCAGT    1740

CTGACAGGCC AATCACGTGG CACAGTAAGA TGTGGTACAT AGTAAGTGCT TAGTAAATAA    1800

TGCAGCACTA GGTAGTT    1817

(2) INFORMATION FOR SEQ ID NO:15:

(i) SEQUENCE CHARACTERISTICS:
        (A) LENGTH: 139 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:15:

```
GCATTTGAAG TGCACCATCA CGGGCCTGAC CTTCTGGGAC CCCAGCTGTG AGGCAGAGGA      60

CAGGGGTGAC AAGTTTGTCT TGCGCAGTGC TTACTCCAGC TGTGGCATGC AGGTGTCAGC     120

AAGTATGATC AGCAATGAG                                                  139
```

(2) INFORMATION FOR SEQ ID NO:16:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:16:

```
GCGGTGGTCA ATATCCTGTC GAGCTCATCA CCACAGCGG                             39
```

(2) INFORMATION FOR SEQ ID NO:17:

(i) SEQUENCE CHARACTERISTICS:
        (A) LENGTH: 313 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:17:

```
GATCGCACCA CTGCACTCCA GCCTGGGCGA CAGAGCGAGA CTCCGTCTCA AAAAAAAAAA      60

AAAAGAGAGT CAGGCAACTC CACAGGGCCA TGATGCCTGT TCCTCCCCAC ACCCCTCGCC     120

CTCCTGGCTG GCGCCGCCAG ATTGACCAAG TCTCCCTCCC GTCCTCCCCC AGAAAAAGGT     180

GCACTGCCTC AACATGGACA GCCTCTCTTT CCAGCTGGGC CTCTACCTCA GCCCACACTT     240

CCTCCAGGCC TCCAACACCA TCGAGCCGGG GCAGCAGAGC TTTGTGCAGG TACCTGGCAT     300

GCCTGTCACC CCT                                                        313
```

(2) INFORMATION FOR SEQ ID NO:18:

(i) SEQUENCE CHARACTERISTICS:
        (A) LENGTH: 654 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:18:

```
TTCCTCTCCG CCTTTCTTCC CACCATGACT CCAGAGGAGA TGAGACTCCC AGAGTCAGGA      60

GGGAGACAGC CTGGGTGCAC AGGGAGAGGG AGAGACAGAG AAGGCATTGC TCAGGGACAC     120

TGACAAGGAT GTGGCCCTGT CCTCCTCCTC TGCCCCAGTA CAGGTCCATG TCTTTCTTTC     180

CACTGTGAGG ACTCAGGGGT GGGAACTCTT AATTCTAGCC GATATTTGAA GGCAGCAGGT     240
```

```
GGGGTGGGGT GAAGAGCAGC TGCCCATGCC GNGTGGCCCT ACCTACCCAT GCAGGTCAGA      300

GTGTCCCCAT CCGTCTCCGA GTTCCTGCTC CAGTTAGACA GCTGCCACCT GGACTTGGGG      360

CCTGAGGGAG GCACCGTGGA ACTCATCCAG GGCCGGGCGG CCAAGGGCAA CTGTGTGAGC      420

CTGCTGTCCC CAAGCCCCGA GGGTGACCCG CGCTTCAGCT TCCTCCTCCA CTTCTACACA      480

GTACCCATAC CCAAAACCGG CACCCTCAGC TGCACGGTAG CCCTGCGTCC CAAGACCGGG      540

TCTCAAGACC AGGTGAGTGG GGCCTGGGCG GCCAGCTTCA AGTGGGAGCT TCCAGGTCTG      600

TGGTTTGCAT GGAAGGGACA TGGCAGCCCA CAGGATGTGG CCAGCTGGTG AGGG           654

(2) INFORMATION FOR SEQ ID NO:19:

(i) SEQUENCE CHARACTERISTICS:
        (A) LENGTH: 319 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:19:

GATCTTCCAG GACTCACCCA GAGGCATCCA GCTACGAAGC GGTGGAGATG GGATTCAAAG       60

CCAAGGCTCT AGGGTGGGCT GGGGTCACGG AGCCAGGGAG TAAACCTGGA AGCCGCCTCC      120

CAAAGGTGCC ACATACTGCT CTCTCTTTCT CCTCCAGGAA GTCCATAGGA CTGTCTTCAT      180

GCGCTTGAAC ATCATCAGCC CTGACCTGTC TGGTGAGCTC CCTCCAGGTC TCTCGGGTTT      240

GTTCTAGTGG CTGAGGTCAC AGTAGGGCAC AGCGGGCAGC CCTGAGAACG GCCTGGCACA      300

TAGCACATGG CAAGGTGGA                                                  319

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:20:

CCTCATAAGG TGGCTGTGAT GATG                                             24

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:21:

CATCTGCCTT GGAGCTTCCT CT                                               22

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA
```

(xi) SEQUENCE DESCRIPTION: SEQ ID NO:22:

TTCCTGACCT CCTACATGG                                              19

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:23:

CTCTTGGTGC CCAAGTTT                                               18

(2) INFORMATION FOR SEQ ID NO:24:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:24:

CGGGCTCTGT TAGGTGCAG                                              19

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:25:

GGGTGGGGCT TTATAAGGGA                                             20

(2) INFORMATION FOR SEQ ID NO:26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:26:

CTGTCCGCTT CAGTGTTCCA TC                                          22

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:27:

GGAAACTTCC CTGATCCAGA GGTT                                        24

-continued (2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:28:

GAGGCCTGGC ATAACCCT                                                   18

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:29:

GTGGCCACTG ATCCAAGG                                                   18

(2) INFORMATION FOR SEQ ID NO:30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:30:

ACACATATCA CACAGTGACC AGC                                      23

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:31:

CTAGGGGAGG AACCAGATGT C                                           21

(2) INFORMATION FOR SEQ ID NO:32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:32:

AGATTGACCA AGTCTCCCTC CC                                         22

(2) INFORMATION FOR SEQ ID NO:33:

(i) SEQUENCE CHARACTERISTICS:
        (A) LENGTH: 22 base pairs
        (B) TYPE: nucleic acid

```
            (C) STRANDEDNESS: single
            (D) TOPOLOGY: linear (ii) MOLECULE TYPE: Genomic DNA (xi) SEQUENCE DESCRIPTION: SEQ ID NO:33:

AGGCTGTCTC CCTCCTGACT CT                                                22

(2) INFORMATION FOR SEQ ID NO:34:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:34:

ACTCAGGGGT GGGAACTCTT                                                   20

(2) INFORMATION FOR SEQ ID NO:35:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:35:

CCTTCCATGC AAACCACAG                                                    19

(2) INFORMATION FOR SEQ ID NO:36:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:36:

GAGTAAACCT GGAAGCCGC                                                    19

(2) INFORMATION FOR SEQ ID NO:37:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:37:

GCCACTAGAA CAAACCCGAG                                                   20

(2) INFORMATION FOR SEQ ID NO:38:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA
```

(xi) SEQUENCE DESCRIPTION: SEQ ID NO:38:

CCAGCACAAC AGGGTAGGGG AT  22

(2) INFORMATION FOR SEQ ID NO:39:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:39:

CTCAGAGGCT TCACTGGGCT CC  22

(2) INFORMATION FOR SEQ ID NO:40:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:40:

TGAAGCCTCT GAGGGATTGA GG  22

(2) INFORMATION FOR SEQ ID NO:41:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:41:

GAGTTCACAC CAGTGCTCCC AG  22

(2) INFORMATION FOR SEQ ID NO:42:

(i) SEQUENCE CHARACTERISTICS:
        (A) LENGTH: 1249 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:42:

CCCTCTAGGT GGACAGTCCT AGCAACCATG GCTCAATNNC AGGCCTGGCT GTGATGAGCC  60

CGTTTGCTGC AAGAGGAGAC TGAGGTTCAG AGAAGTCGAG GGTCCATGGC TCAGCAGAGC  120

TGGCACCAAA CCCACATGGG CCAGCACAAC AGGGTAGGGG ATGGGCAGG GGCAGAGTGG  180

CAGTGCTGAT GGCGTCGGCC CTCTCTAGGT TGCACAAGCA AAGGCCTCGT CCTGCCCGCC  240

GTGCTGGGCA TCACCTTTGG TGCCTTCCTC ATCGGGGCCC TGCTCACTGC TGCACTCTGG  300

TACATCTACT CGCACACGCG TGAGTACCCC AGGCCCCCAC AGTGAGCATG CCGGGCCCCT  360

CCATCCACCC GGGGGAGCCC AGTGAAGCCT CTGAGGGATT GAGGGGCCCT GGCAGGACCC  420

TGACCTCCGC CCCTGCCCCC GCTCCCGCTC CCAGGTTCCC CCAGCAAGCG GGAGCCCGTG  480

GTGGCGGTGG CTGCCCCGGC CTCCTCGGAG AGCAGCAGCA CCAACCACAG CATCGGGAGC  540

```
ACCCAGAGCA CCCCCTGCTC CACCAGCAGC ATGGCATAGC CCCGGCCCCC CGCGCTCGCC      600

CAGCAGGAGA GACTGAGCAG CCGCCAGCTG GGAGCACTGG TGTGAACTCA CCCTGGGAGC      660

CAGTCCTCCA CTCGACCCAG AATGGAGCCT GCTCTCCGCG CCTACCCTTC CCGCCTCCCT      720

CTCAGAGGCC TGCTGCCAGT GCAGCCACTG GCTTGGAACA CCTTGGGGTC CCTCCACCCC      780

ACAGAACCTT CAACCCAGTG GGTCTGGGAT ATGGCTGCCC AGGAGACAGA CCACTTGCCA      840

CGCTGTTGTA AAAACCCAAG TCCCTGTCAT TTGAACCTGG ATCCAGCACT GGTGAACTGA      900

GCTGGGCAGG AAGGGAGAAC TTGAAACAGA TTCAGGCCAG CCCAGCCAGG CCAACAGCAC      960

CTCCCCGCTG GGAAGAGAAG AGGGCCCAGC CCAGAGCCAC CTGGATCTAT CCCTGCGGCC     1020

TCCACACCTG AACTTGCCTA ACTAACTGGC AGGGGAGACA GGAGCCTAGC GGAGCCCAGC     1080

CTGGGAGCCC AGAGGGTGGC AAGAACAGTG GGCGTTGGGA GCCTAGCTCC TGCCACATGG     1140

AGCCCCCTCT GCCGGTCGGG CAGCCAGCAG AGGGGGAGTA GCCAAGCTGC TTGTCCTGGG     1200

CCTGCCCCTG TGTATTCACC ACCAATAAAT CAGACCATGA AACCTGAAA               1249
```